US011938298B2

(12) United States Patent
Horlock

(10) Patent No.: US 11,938,298 B2
(45) Date of Patent: Mar. 26, 2024

(54) MEDICAL INJECTION DEVICE PACKAGING

(71) Applicant: Teva Pharmaecutical Industries Ltd., Petah Tiqva (IL)

(72) Inventor: Mark Horlock, Timperley (GB)

(73) Assignee: Teva Pharmaecutical Industries Ltd., Petah Tiqva (IL)

( * ) Notice: Subject to any disclaimer, the term of this patent is extended or adjusted under 35 U.S.C. 154(b) by 0 days.

(21) Appl. No.: 18/144,233

(22) Filed: May 7, 2023

(65) Prior Publication Data

US 2023/0302216 A1    Sep. 28, 2023

Related U.S. Application Data

(63) Continuation of application No. 15/840,150, filed on Dec. 13, 2017, now Pat. No. 11,642,451.

(30) Foreign Application Priority Data

Dec. 14, 2016  (GB) ...................... 1621275

(51) Int. Cl.
*A61M 5/00* (2006.01)

(52) U.S. Cl.
CPC ............ *A61M 5/002* (2013.01); *A61M 5/008* (2013.01); *A61M 2209/06* (2013.01)

(58) Field of Classification Search
CPC .. A61M 5/002; A61M 5/008; A61M 2209/06; A61B 17/06114; B65D 1/36;
(Continued)

(56) References Cited

U.S. PATENT DOCUMENTS 4,783,874 A * 11/1988 Perches .................... A46B 7/02
                                                                                           15/167.1
5,522,503 A *  6/1996 Halbich ................ A61M 5/002
                                                                                           220/837
(Continued)

FOREIGN PATENT DOCUMENTS

JP       H11155948 A    6/1999
WO       9927971 A2     6/1999
(Continued)

OTHER PUBLICATIONS

Physician's Desk Reference, "Copaxone", 2005, Medical Economics Co., Inc., Montvale, N.J., 3115; 6 pages.

*Primary Examiner* — Javier A Pagan
(74) *Attorney, Agent, or Firm* — Blank Rome LLP

(57) ABSTRACT

A kit including a packaging and an injection device is described. The injection device defines a positioning recess. The packaging includes a channel extending longitudinally to accommodate the injection device. The channel includes a first longitudinal wall, a second longitudinal wall opposing the first longitudinal wall, and a base wall extending between the first longitudinal wall and the second longitudinal wall. The packaging also includes a first handling recess defined by the first longitudinal wall and a second handling recess defined by the second longitudinal wall. The packaging also includes a positioning rib protruding from the base wall into the channel for insertion into the positioning recess of the injection device.

29 Claims, 10 Drawing Sheets

(58) Field of Classification Search
CPC ...... B65D 81/33; B65D 85/20; B65D 5/5076; B65D 5/323; B65D 5/5324; B65D 5/5071; B65D 5/4204; B65D 25/005
USPC .................................. 206/364, 587, 583, 594
See application file for complete search history.

(56) References Cited

U.S. PATENT DOCUMENTS

| | | | |
|---|---|---|---|
| 5,611,432 A * | 3/1997 | Dods | B65D 75/366 |
| | | | 206/459.5 |
| 6,090,382 A | 7/2000 | Salfeld et al. | |
| 6,216,885 B1 * | 4/2001 | Guillaume | B65D 71/70 |
| | | | 206/564 |
| 7,308,985 B2 * | 12/2007 | Riley | A61B 50/30 |
| | | | 206/363 |
| 7,441,655 B1 * | 10/2008 | Hoftman | A61B 50/20 |
| | | | 206/370 |
| 9,528,208 B2 * | 12/2016 | Keene | D04H 3/011 |
| 2010/0160894 A1 * | 6/2010 | Julian | A61P 19/02 |
| | | | 434/262 |
| 2014/0078854 A1 * | 3/2014 | Head | B01F 31/20 |
| | | | 206/364 |
| 2016/0271320 A1 | 9/2016 | Le Maner | |
| 2017/0072142 A1 * | 3/2017 | Perthu | A61M 5/3202 |

FOREIGN PATENT DOCUMENTS

| | | |
|---|---|---|
| WO | 2007054809 A2 | 5/2007 |
| WO | 2013176703 A1 | 11/2013 |
| WO | 2015131903 A1 | 9/2015 |

* cited by examiner
MEDICAL INJECTION DEVICE PACKAGING

CROSS-REFERENCE TO RELATED APPLICATIONS

This application is a continuation application if U.S. patent application Ser. No. 15/840,150, filed Dec. 13, 2017, which claims the benefit of Great Britain Patent App. No. 1621275.5, filed Dec. 14, 2016, the disclosures of which are incorporated herein by reference in their entirety.

TECHNICAL FIELD

The present disclosure relates generally to the field of medical packaging for containing medical injection devices and in particular medical tray type packaging for containing said devices.

BACKGROUND

Medical tray type packaging of the type for containing a medical injection device commonly comprises a thermoformed tray formed from a plastic sheet. The plastic sheet is formed to extend around the device. To close the tray a tear away or break through lid may be provided as medical blister type packaging. Alternatively, the lid formed of a corresponding plastic sheet may be arranged as medical clamshell type packaging.

Medical tray type packaging may differ from traditional pharmaceutical blister packaging for unit-dose packaging of tablets in that, for protection of the device, the tray is not collapsible. The device therefore cannot be pushed-though for extraction. Consequently, a process for extraction of a device from a tray can be more complex. It may comprise removal/perforation of the lid and a user reaching into part of the channel and gripping the device. The channel may be narrow and difficult to access, particularly for users who have and illness reducing their dexterity.

In spite of the effort already invested in the development of said packaging, further improvements are desirable.

BRIEF DESCRIPTION OF THE FIGURES

Aspects, features and advantages of embodiments of the present disclosure will become apparent from the following description of embodiments in reference to the appended drawings in which like numerals denote like elements.

DETAILED DESCRIPTION OF EMBODIMENTS

Figure 1:
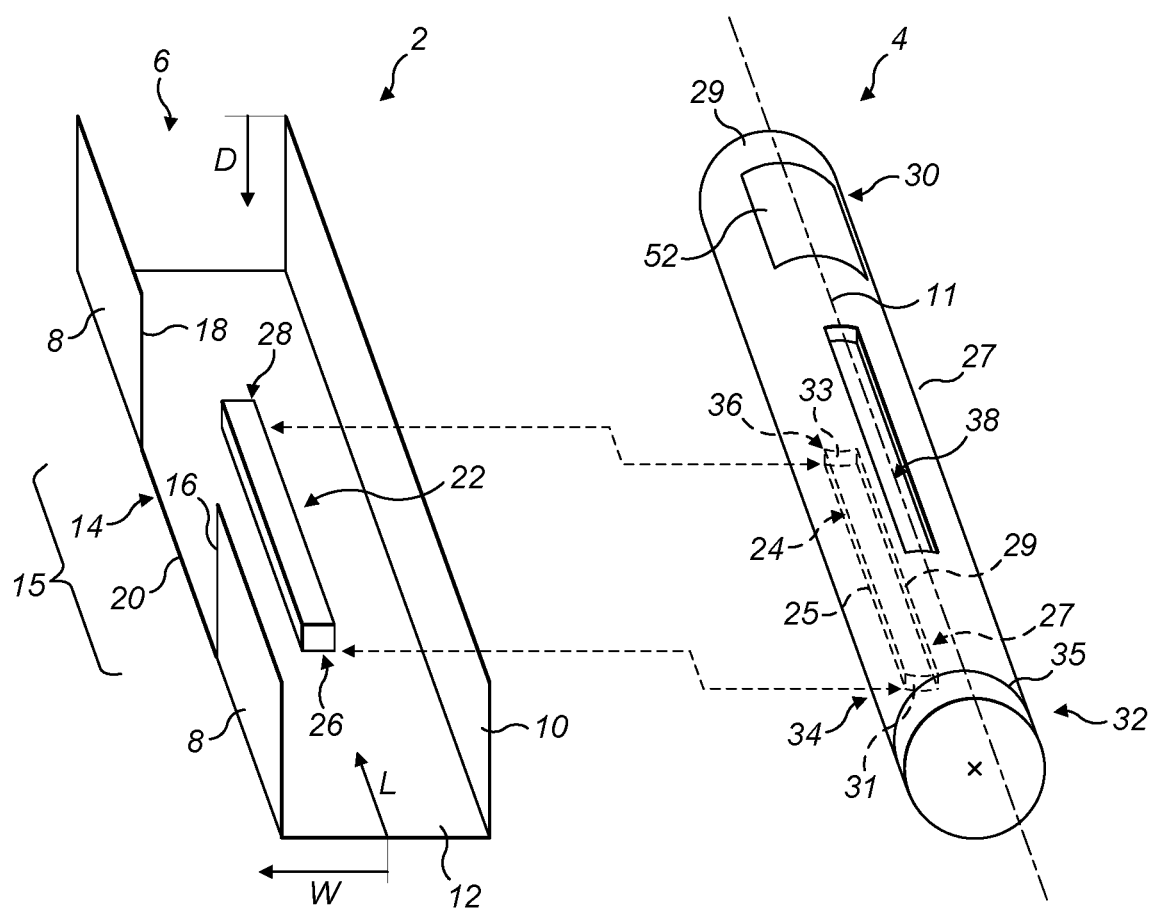
FIG. 1 is an exploded schematic perspective diagram showing an embodiment packaging and an embodiment injection device, wherein a positioning recess of the injection device is shown in hidden line.

Before describing embodiments of the packaging, it is to be understood that the packing is not limited to the details of construction or process steps set forth in the following description. It will be apparent to those skilled in the art having the benefit of the present disclosure that the packaging is capable of other embodiments and of being practiced or being carried out in various ways. Accordingly, the embodiments are merely examples and should not be construed to narrow the scope or spirit of the subject matter described herein in any way. Moreover, the embodiments may be combined in any suitable combination to provide further embodiments.

The present disclosure may be better understood in view of the following explanations:

As used herein, the terms "package" or "packaging" may encompass any arrangement to wrap or protect an injection device. Packaging can be rigid or flexible. Packaging may include blister packs, medical clamshell, clamshell trays, medical trays and other like arrangements. The packaging may be sterile or nonsterile.

As used herein, the term "Injection device" may include a device for the injection of a medicament to a body of a human or animal subject and includes devices configured for various delivery methods, such as intradermal, subcutaneous, intramuscular, intravenous, intraosseous, intraperitoneal, intrathecal, epidural, intracardiac, intraarticular, intracavernous, intravitreal or other like method. Injection device includes syringes of all types, devices that contain said syringes such as auto-injectors, pen-injectors and other like devices.

As used herein, the term "auto-injector" may include any device configured to deliver a dose of a medicament from a prefilled syringe. The auto-injector may be configured to deliver a single dose of a medicament. Auto-injectors may include a device comprising a prefilled syringe that contains a medicament. The prefilled syringe may be embedded in the auto-injector, for example for a disposable device. In other embodiments, the prefilled syringe may be insertable in and removable from the auto-injector, for example for a multi-use device. The syringe may be spring, gas or otherwise actuated for said delivery. A presently available example is the DAI™ by SHL Group and the Ypsomate™ by Ypsomed.

As used herein, the term "pen-injector" may include any device configured to deliver a dose of a medicament from a cartridge. The delivery may be via spring, gas or otherwise actuated.

As used herein, the terms "grip" or "gripping" may include to hold by clasping or grasping with digits of hands of a user with a pincer type action. Grip includes a manner of gripping suitable for removing an injection device as defined herein from a channel as defined herein. Grip includes a user's opposed digits pressing against the injection device such that frictional forces are greater that the weight of the injection device or the force retaining the injection device in the channel.

The term "digits" may include reference to one or two fingers and an opposed thumb. The fingers are typically selected from the index finger, middle finger, ring finger. The size of user's fingers and thumb are within conventionally accepted ranges. In an example, user fingers and thumbs may be idealised as having a hemispherical tip that extends into a nominal circular cross-sectioned body. For fingers the body may have a diameter that may be 10-20 mm. For thumbs the body may have a diameter that may be 10-30 mm. Further hand dimensions may be as defined by http://usability.gtri.gatech.edu/eou_info/hand_anthro.php or similar hand/finger anthropometry study.

As used herein "user" is intended to refer to a healthcare professional, a medical practitioner, human end user or other human user associated therewith.

As used herein, the term "medicament" may include a substance, which may be in liquid form. The medicament can include a substance for use in the treatment or prevention of a disorder that causes reduced dexterity of a user, examples include multiple sclerosis, rheumatoid arthritis, muscular atrophy, Parkinson's disease, celiac disease, Alzheimer's disease.

In an embodiment medicament comprises Glatiramer acetate (GA). GA is a mixture of polypeptides which do not all have the same amino acid sequence GA is marketed under the tradename Copaxone®. GA comprises the acetate salts of polypeptides containing L-glutamic acid, L-alanine, L-tyrosine and L-lysine at average molar fractions of 0.141, 0.427, 0.095 and 0.338, respectively. The average molecular weight of Copaxone® is between 5,000 and 9,000 daltons. ("Copaxone", Physician's Desk Reference, (2005), Medical Economics Co., Inc., (Montvale, N.J.), 3115.) Chemically, glatiramer acetate is designated L-glutamic acid polymer with L-alanine, L-lysine, L-tyrosine, acetate (salt).

In an embodiment medicament comprises an anti-TNFα antibody, preferably the anti-TNFα antibody is adalimumab. Adalimumab is marketed under the trade name Humira® and is described in U.S. Pat. No. 6,090,382.

In an embodiment the medicament comprises Follicle-stimulating hormone (FSH), also known as follitropin alfa. FHS is for the treatment of infertility. FSH is marketed under the following brands: Ovaleap® (Teva Pharma); Gonal-f® (Merck Serono); Puregon (Merck Sharp and Dohme), Bemfola (Finox Biotech), Elonva (Merck Sharp and Dohme). FSH is for use in the treatment of the following indications: anovulation (including polycystic ovarian syndrome) in women who have been unresponsive to treatment with clomifene citrate; stimulation of mutifollicular development in women undergoing superovulation for assisted reproductive technologies (ART) such as in vitro fertilisation (IVF), gamete intra-fallopian transfer and zygote intra-fallopian transfer; FSH in association with a luteinising hormone (LH) preparation is for the stimulation of follicular development in women with severe LH and FSH deficiency, in clinical trials these patients were defined by an endogenous serum LH level <1.2 IU/L; FSH is for use in the stimulation of spermatogenesis in men who have congenital or acquired hypogonadotropic hypogonadism with concomitant human chorionic gonadotropin (hCG) therapy.

In an embodiment the medicament comprises Reslizumab. Reslizumab is marketed as Cinqair®. Reslizumab is an interleukin-5 antagonist monoclonal antibody (IgG4 kappa) for use in add-on maintenance treatment of patients with severe asthma aged 18 years and older, and with an eosinophilic phenotype (1). Reslizumab is an FDA approved antibody. The market authorisation holder is Teva Respiratory LLC.

In an embodiment the medicament comprises an anti-CGRP antibody, which may be referred to as Fremanusumab. The anti-CGRP antibody may be produced by expression vectors having deposit numbers of ATCC PTA-6867 and ATCC PTA-6866 as disclosed in application WO2007054809.

As used herein, the term "contiguous" may refer to a close proximity, including within 1-2 mm or 1-4 mm or other amount, without actually touching.

As used herein, the term "channel" may include a cut-out or groove like portion of the packaging that provides a containing function in respect of the injection device. The channel may include a U-section, V-section or other suitably profiled section. The channel may extend around a portion of an accommodated injection device to cover the portion of said device. The channel may be arranged to abut and/or to be contiguous an accommodated injection device. The channel may substantially conform to the shape of the injection device. The channel may be formed with longitudinal walls adjoined by a base wall. A base wall of the channel can be distinguished from a longitudinal/lateral wall by a portion of the channel that comprises a directional vector of extension with a longitudinal/lateral component greater than a depth component.

As used herein, the term "recess" may include a cut-out or groove like portion of the packaging. In embodiments a handling recess may be arranged to provide user access, via one or more digits of a hand of a user, to a depth position of the channel to enable gripping of an injection device accommodated in the channel. The handling recess may be arranged adjacent to and extend orthogonal the channel (and therefore an accommodated injection device). In embodiments a positioning recess is arranged to receive a rib of the channel to locate the device in the channel. The recess may include a U-section, V-section or other suitably profiled section. The recess can be formed with longitudinal/lateral walls adjoined by an adjoining wall. An adjoining wall of the recess can herein be distinguished from a longitudinal/lateral wall by a portion of the recess that comprises a directional vector of extension with a lateral/longitudinal component greater than a depth component.

As used herein, the term "longitudinal" refers to a direction aligned to a length of the channel, and thus a longitudinal axis of an accommodated injection device.

As used herein, the term "lateral" refers to a direction aligned to a width of the channel, and thus a width of an accommodated injection device. The lateral direction is orthogonal to the longitudinal direction.

As used herein, the term "depth" refers to a direction aligned to a depth of the channel, and thus a depth of an accommodated injection device. The depth direction refers to the depth of the packaging when viewed from a packaging planform in a laterally and longitudinally extending plane.

In the accompanying figures the longitudinal, lateral and depth directions are designated by respective 'L', 'W' and 'D'.

The term "above" with reference to the packaging refers to a position located above the planform when viewed in the depth direction. The term "below" with reference to the packaging refers to a position located below a base of the packaging when viewed in the opposed depth direction. The term "top" refers to a portion of the packaging that forms part of the planform when viewed from above. The term "bottom" refers to a portion of the packaging that abuts a support surface, such as a table, when the injection device is to be extracted from the channel.

The terms "proximal" and "distal" when used in reference to the injection device refer to a longitudinal position in respect of a delivery end of the device. When used in reference to the packaging they refer to a longitudinal position associated with the delivery end of an injection device accommodated in the channel.

The term "concave" when used in reference to the formation of the packaging may refer to a surface that is arranged to extend inwardly, including curved (e.g., a C-shape) and/or linear (e.g., a U-shape). The term "convex" when used in reference to the formation of the packaging may refer to a surface that is arranged to extend inwardly, including curved (e.g., a C-shape) and/or linear (e.g., a U-shape).

The present disclosure provides packaging suitable for a medical injection device, which includes suitability in that the packaging is dimensioned to accommodate a typical injection device, and thus includes suitability for injection training devices with dimensions corresponding to those of the associated injection device. Suitability for a medical injection device also includes that the packaging may be certified to various standards for leakage, ageing and porosity. Said standards may include the US Food and Drugs Association (FDA) Consensus Standards, as defined by the Institute of Packaging Professionals, Medical device Packaging Technical Committee, including D3078:1994; F1608:2000; and F1980:2002.

Figure 2:
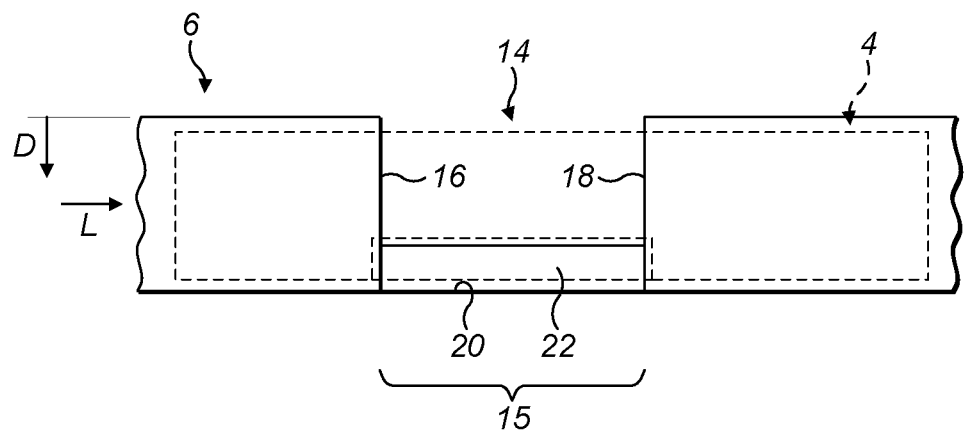
FIG. 2 is a side schematic diagram showing the embodiment packaging of FIG. 1 accommodating the injection device of FIG. 1, wherein the injection device is shown in hidden line.

Referring to FIG. 1 and FIG. 2, embodiment packaging 2 for an injection device 4 comprises a channel 6 that extends in the longitudinal direction L to accommodate the injection device. The channel 6 is formed by a first longitudinal wall 8 and a second longitudinal wall 10, which are interposed by an adjoining base wall 12.

A handling recess 14 enables handling of the injection device 4 accommodated in the channel 6. The handling recess 14 extends in the lateral direction and is formed through the first longitudinal wall 8.

A positioning rib 22 is arranged to protrude from the base wall 12 into the channel 6. The positioning rib 22 is adapted to position the injection device 4 in the channel 6 via insertion into a complementary positioning recess 24 of the injection device 4.

The positioning rib 22 is arranged offset laterally from the handling recess 14. In respect of the positioning rib arranged offset laterally from the handling recess 14, meant that the rib occupies a distinct lateral position from that of the handling recess, e.g., there is a portion of the base wall 12 of the channel 6 arranged therebetween.

The positioning rib 22 is arranged extending in a longitudinal field 15 defined by the handling recess 14. By arranged within (or extending in) a longitudinal field it is meant that part or all of the positioning rib 22 occupies the same longitudinal position as the handling recess 14. The handling recess 14 thus defines a longitudinal field/locus that is bounded/marked off by the longitudinal extremities of the handling recess.

The injection device 4 and channel 6 are complementary in shape such that the injection device 4 can be suitably accommodated in the channel 6.

The injection device 4 includes a body 29, which extends longitudinally between a distal end 30 and proximal end 32, the proximal end 32 is adapted for delivery of the medicament. Said adaptation may comprises a subcutaneous delivery member (not shown) or a connector (an example includes a Luer connector) for receiving said member or other suitable configuration. Example of subcutaneous delivery members include a hypodermic needle. A removable end cap 35 may be arranged at the proximal end 32 to protect the subcutaneous delivery member.

The injection device 4 includes the positioning recess 24 arranged in the body 29 to extend in the longitudinal direction between the distal end 30 and proximal end 32. The positioning recess 24 includes a first recess end 34 and a second recess end 36. The positioning recess 24 is complementary in shape to the positioning rib 22. The first recess end 34 and second recess end 36 are longitudinally disposed to receive in abutment and/or contiguously a corresponding first rib end 26 and second rib end 28 of the positioning rib 22.

The positioning recess 24 includes first longitudinal wall 25, a second longitudinal wall 27 adjoined by a base wall 29. The first recess end 34 and a second recess end 36 comprise a respective distal lateral 31 and a proximal lateral wall 33 that adjoins the walls 25, 27 and 29. The walls 25, 27, 29, 31 that form the sides and ends of the positioning rib are generally planar, although alternative configurations are included in the disclosure, including curved. The configuration of said walls of the positioning recess generally corresponds to those of the positioning rib 22 as will be discussed.

The positioning recess 24 includes a delivery window for visual feedback of medicament delivery. The delivery window is formed as at least part of a base wall 29 of the positioning recess 24.

The injection device 4 includes a further positioning recess 38 corresponding to the positioning recess 24 (the disclosure also includes embodiments with a single such recess). The further positioning recess 38 is arranged on the body 29 longitudinally aligned and opposed to the positioning recess 24. With one of the positioning recesses 24, 38 receiving the positioning rib 22 of the packaging 2, the delivery window of the other positioning recess 24, 38 can be observed when viewing from the planform of the packaging 2. A user may be notified of the operative state of the injection device before/whilst removing the injective device 4 from the packaging 2.

The injection device 4 includes a label 52 arranged on the body 29. The label 52 may include instructions for operation of the injection device (IFU) and/or a dosage regimen selected for the medicament. The label 52 is arranged relative to the or each positioning recess 24, 38 to be visible when viewing the planform of the packaging 2 accommodating the device 4. For example, the label 52 is orientated equidistantly (or approximately equidistantly, which may include an offset of ±10 or 20%) about a longitudinal axis 11 that extends through a positioning recess 24, 38 or is otherwise suitably arranged. A user may thus be notified of the label before/whilst removing the injection device 4 from the packaging 2. The label 52 is arranged at a different longitudinal position to the positioning recess 24, 38. Since the positioning recess is aligned to the handling recess 14, it is ensured that a user does not obscure the label when gripping an accommodated device 4. The disclosure includes embodiments with alternatively arranged label. A label may refer to a portion of material adhered to the body, or otherwise attached thereto. A label may be formed in the body by printing, embossing, moulding, stamping or otherwise.

The handling recess 14 is arranged to ensure the proximal end 32 of the injection device 4 is not gripped during extraction. Gripping of the proximal end 32 may result in one or more of: damage to the user; damage to the subcutaneous delivery member; dislodging of the end cap. In other embodiments the handing recess 14 can be arranged to control gripping at any part of the injection device 4.

In embodiments the injection device 4 may be replaced with a corresponding injection device training device, which can include the same components, geometric shape of the injection device and operability but without medicament delivery capability. Typically the device is dimensioned with a longitudinal length of 10-30 cm and a cross-sectional area of 0.8-20 cm².

Figure 3:
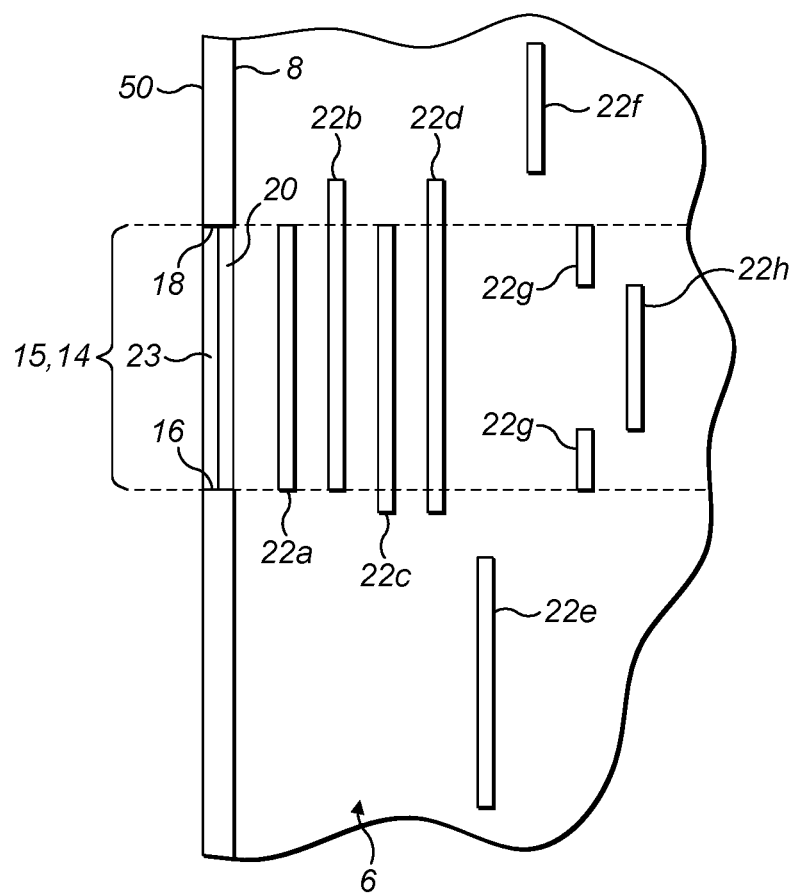
FIG. 3 is a plan schematic diagram showing embodiments of the packaging of FIG. 1.

Referring to FIG. 3 embodiment arrangements of the positioning rib with respect to the longitudinal field 15 include: the positioning rib 22a with both ends aligned to the periphery of the longitudinal field 15; the positioning rib 22b, 22c with one end aligned to the periphery of the longitudinal field 15 and the other arranged outside of the longitudinal field 15; the positioning rib 22d with both ends arranged outside of the longitudinal field 15 and the rib extending in the longitudinal field 15; the positioning rib 22e, 22f with both ends arranged outside of the longitudinal field 15 and the rib extending outside the longitudinal field 15; the positioning rib 22g with both ends aligned to the periphery of the longitudinal field 15 and formed of several protrusions; the positioning rib 22h with neither end aligned to the periphery of the longitudinal field 15 and arranged within of the longitudinal field 15. It will be understood that in such embodiments the positioning recess 26 is correspondingly arranged to locate the ends of the injection device 4 in the desired position in the channel 6.

With further reference to FIGS. 1 and 2, the handling recess 14 is formed by a first lateral wall 16 and a second lateral wall 18, which are interposed by an adjoining wall 20. The positioning rib 22 comprises a first rib end 26 and second rib end 28 and extends laterally therebetween.

The first rib 26 end and second rib end 28 are aligned in the longitudinal direction to the respective first lateral wall 16 and second lateral 18 wall of the handling recess 14. The positioning rib 22 is therefore arranged entirely within the longitudinal field 15 of the handling recess 14.

In respect of the first rib end 26 and second rib end 28 arranged aligned longitudinally to the respective first lateral wall 16 and second lateral wall 18 of the handling recess 14, it is to be understood that a portion that forms an end lateral wall of the rib, which may include a portion interconnecting the rib and base wall 12 of the channel 6 or a portion interconnecting the end lateral wall of the rib with a top adjoining wall of the rib (e.g. a round or chamfered or other like connection), overlaps a longitudinal position of part of the associated lateral wall 16, 18.

In embodiments with an inclined first lateral wall 16 and/or an inclined second lateral wall 18 (an example of which is shown in the embodiment of FIGS. 3-6) it is to be understood that the associated rib end can be longitudinally aligned to a longitudinal field 15 that spans the longitudinal distance of the incline.

In variant embodiments, one or both of the first rib end 26 and second rib end 28 are arranged outside of the longitudinal field 15 defined by the handling recess 14. The positioning rib 22 thus has a greater longitudinal length than the longitudinal field 15 of the handling recess 14. In an embodiment, one or both of the first rib end 26 and second rib end 28 are arranged within the longitudinal field 15 of the handling recess 14 and aligned to the adjoining wall 20 of the handling recess 14. The positioning rib 22 thus has a lesser longitudinal length than the longitudinal field 15 of the handling recess 14.

Referring to FIG. 4-13 an example comprises features within the scope of the preceding embodiments. The channel 6 includes the first longitudinal wall 8 and second longitudinal wall 10 arranged to extend along inclined planes that intersect at an apex arranged depth D below a base of the packaging 2. The inclined planes are truncated by the adjoining base wall 12. The inclination of the planes relative to the depth direction is 2-5°, however in other embodiments it may be 2-20° or other suitable amount. The adjoining base wall 12 is generally aligned in a plane extending in the longitudinal L and lateral W directions. Thus the channel 6 has a generally truncated V-shaped cross-section. The longitudinal walls 8, 10 and base wall 12 may adjoin along a straight edge or with a round, which may have a radius of 0.5-4 mm, or other profile including a chamfer.

In variant embodiments, which are not illustrated, the channel may have other suitable sections. One example is a U-shaped section, wherein first longitudinal wall and second longitudinal wall arranged aligned to each other and to the depth direction. Another example is a section which is profiled to conform to that of the injection device, e.g., a partially circular or curved cross section to conform to that of the embodiment injection device shown in FIG. 1. In such an example the section may follow that of the injection device such that it is either in abutment or continuous thereto. In other embodiments the aforedescribed channel sections may be combined.

Figure 6:
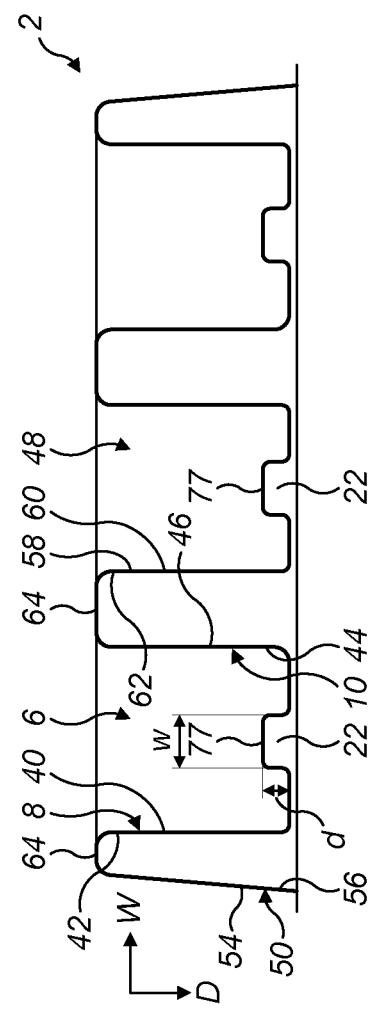
FIG. 6 is a front sectional view showing the embodiment packaging of FIG. 4.

Referring to FIG. 6, the first longitudinal wall 8 includes a first face 40, which faces the channel 6, and a second face 42, which faces away from the channel 6. The second longitudinal wall 10 includes a first face 44, which faces the channel 6, and a second face 46, which faces away from the channel 6.

A peripheral longitudinal wall 50 is arranged adjacent the first longitudinal wall 8. The peripheral longitudinal wall 50 forms a peripheral wall of the packaging 2. The peripheral longitudinal wall 50, comprises a first face 54, which faces away from channel 6, and a second face 56, which faces the channel 6. The peripheral longitudinal wall 50 is inclined to the first longitudinal wall 8, such that both walls extend along inclined planes that intersect at an apex arranged above the packaging 2. The inclination of the planes relative to the depth direction may be 1-5° or other amount. The inclined planes are truncated by a top adjoining wall 64, which adjoins the peripheral longitudinal wall 50 first longitudinal wall 8. The inclination of the walls 8, 50 may aid in stacking, in the depth direction, of like packaging.

An additional first longitudinal wall 58 is arranged adjacent the second longitudinal wall 10. The first longitudinal wall 58 forms an adjacent channel 48 for accommodating a further injection device. In the embodiment three such channels are provided. The first longitudinal wall 58, comprises a first face 60, which faces the channel 48, and a second face 62, which faces away from the channel 48. The first longitudinal wall 58 is inclined to the second longitudinal wall 10, such that both walls extend along inclined planes that intersect at an apex arranged above the packaging 2. The inclination of the planes relative to the depth direction may be 1-5° or other amount. The inclined planes are truncated by a top adjoining wall 64, which adjoins the first longitudinal wall 58 and second longitudinal wall 10. The inclination of the walls 10, 58 may aid in stacking, in the depth direction, of like packaging.

The adjacent channel 48 and further channel and associated forming walls may comprise a similar configuration to that of the channel 8, thus for brevity they are not described herein. For convenience the peripheral longitudinal wall 50 and first longitudinal wall 58 may be referred to generally as a further longitudinal wall when referring to the channel 8.

In variant embodiments, which are not illustrated, there may be any suitable number of channels for accommodation of injection devices, including 1-6. The peripheral wall and/or first longitudinal wall adjacent the second longitudinal wall may be omitted, e.g., in an embodiment with only a single channel. In embodiments when present they may be alternatively arranged, including aligned in the depth direction.

Figure 5:
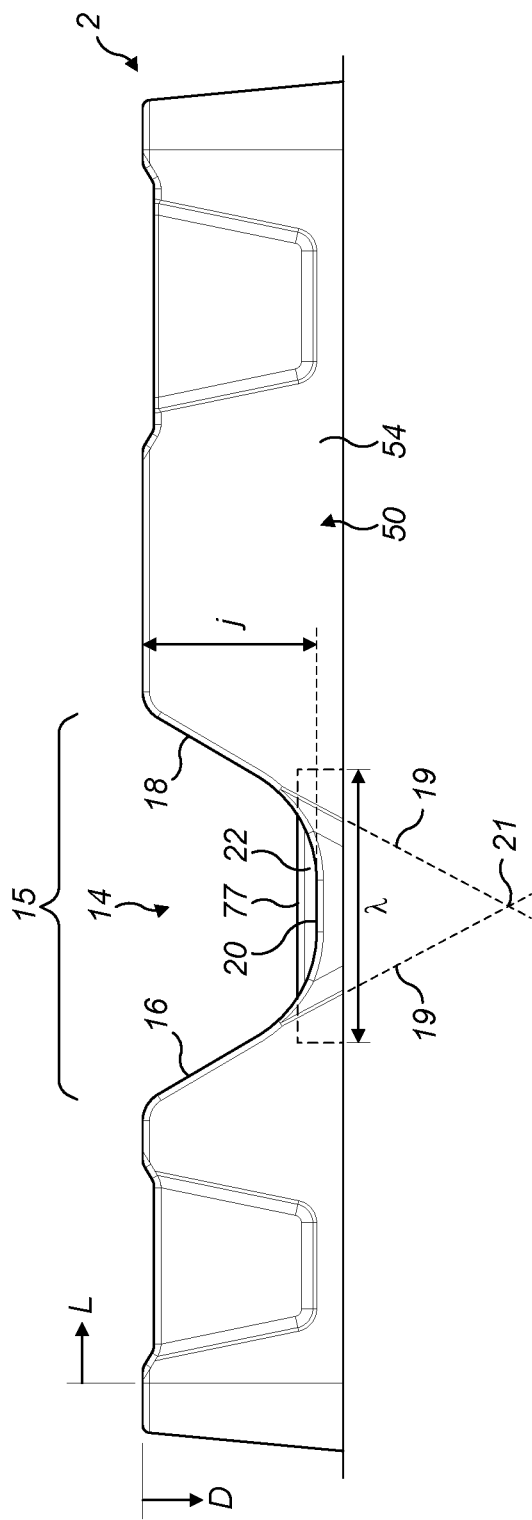
FIG. 5 is a side view showing the embodiment packaging of FIG. 4.

Referring to FIG. 5, the first lateral wall 16 and the second lateral wall 18 of the handling recess 14 extend along inclined planes 19 that intersect at an apex 21. The apex 21 is arranged below the packaging 2, e.g., a base thereof. The extension of the lateral walls 16, 18 is truncated by the adjoining wall 20. The inclination of the planes 19 relative to the depth direction may be 30-55° or other amount. The inclination of the lateral walls 16, 18 provides a wider mouth at a top of the handling recess 14, which may aid a user when inserting a digit into said recess, e.g. by providing a shape that corresponds to the digit and/or by guiding the digit to a central location of the handling recess from which it is most appropriate to grip the injection device 4. The inclination of the lateral walls 16, 18 (compared to lateral walls that extend from the same mouth separation and that are aligned in the depth direction) may provide a rigid region proximal the adjoining wall 20.

The lateral walls 16, 18 adjoin the adjoining wall 20 with a round, which may have a radius of 5-20 cm or other amount. The round may provide a more rigid region proximal the adjoining wall 20 and may conform to a shape of a digit of a user.

The base wall 12 of the channel 6 has a greater depth than the adjoining wall 20 of the handling recess 14. The base wall thus forms a reinforcing rib that extends in the longitudinal direction and protrudes in the opposed depth direction adjacent the channel 6. Such an arrangement may provide a rigid region proximal the adjoining wall 20, when compared to an embodiment (which is also included in the disclosure) wherein the base wall 12 of the channel 6 has the same depth as the adjoining wall 20 of the handling recess 14.

In variant embodiments, which are not illustrated, the first and second lateral walls 16, 18 may be alternatively arranged, including aligned in the depth direction. The adjoining wall 20 may be alternatively arranged, including arranged at the same depth as and/or inclined to the base wall 12. One or more of the adjoining wall 20, first and second lateral walls 16, 18 may be alternatively profiled, including curved or stepped or straight edged.

Referring to FIG. 3, in an embodiment the adjoining wall 20 may include a reinforcing rib 23 protruding into the handling recess 14. The reinforcing rib 23 may provide additional stiffening of the handling recess 14. The reinforcing rib 23 extends longitudinally from the first and second lateral walls 16, 18. The reinforcing rib 23 is laterally offset from the first longitudinal wall 8. The offset may enable a user to more conveniently insert their digits into the handling recess 14 to grip the injection device 4. The reinforcing rib 23 has a lateral width of less than between the first longitudinal wall 8 and second longitudinal wall 50. In variant embodiments, which are not illustrated, the reinforcing rib may be alternatively arranged, including centrally aligned and extending from only one of the first and second lateral walls 16, 18.

Figure 7:
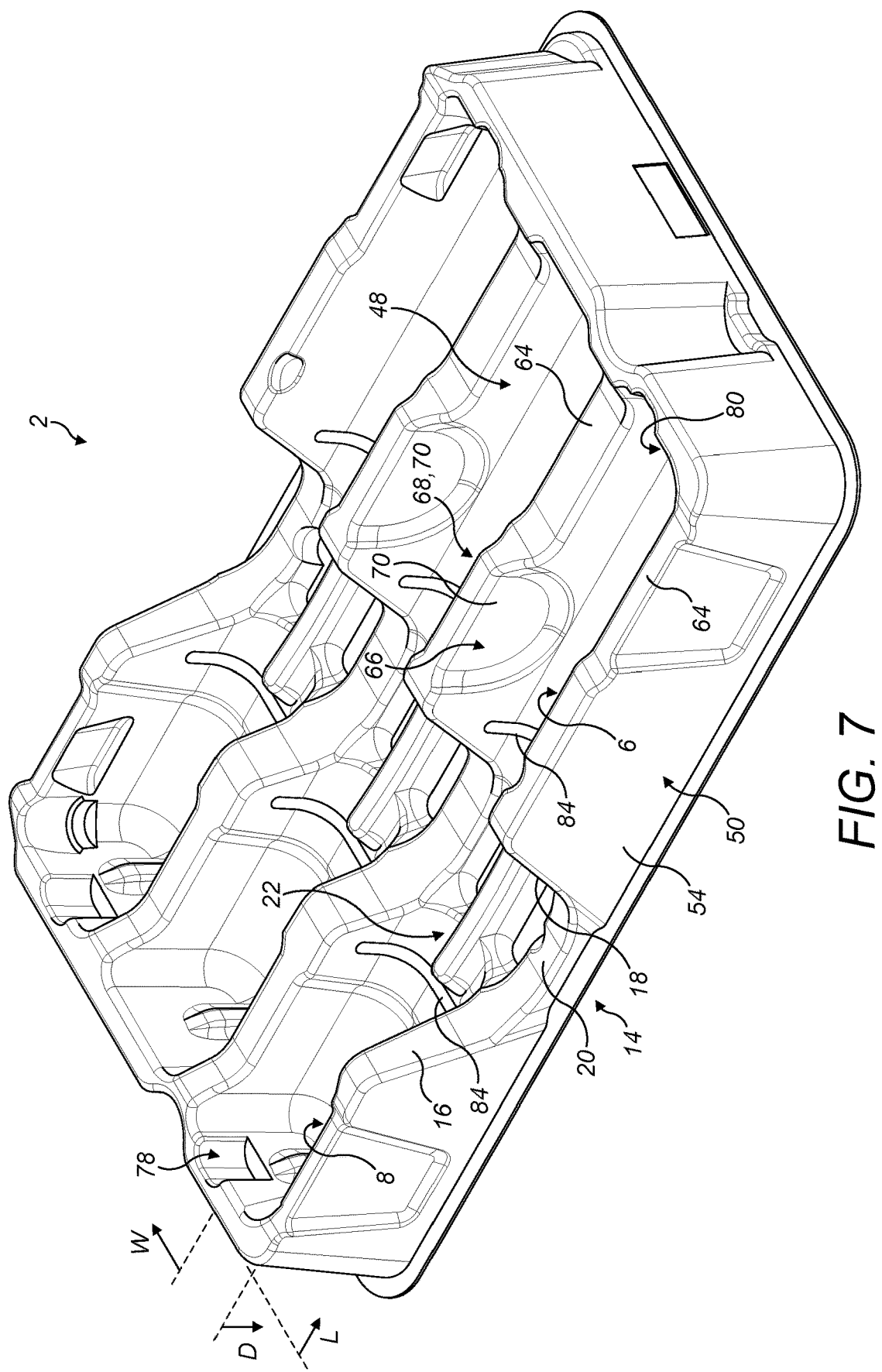
FIG. 7 is a perspective view showing the embodiment packaging of FIG. 4.

Referring to FIG. 7, the handling recess 14 is formed through the further longitudinal wall 50 (in addition to the previously discussed first longitudinal wall 8) the first and second lateral walls 16, 18 and adjoining wall 20 thus bridge said longitudinal walls. Such an arrangement may provide a handling recess 14 which has enhanced rigidity compared to an arrangement without said bridging.

The packaging includes a second handling recess 82. The second handling recess 82 is formed through the first longitudinal wall 58 and second longitudinal wall 10. The second handling recess 82 is complementary to the handling recess 14, and is thus comprises like components, which for brevity are not described. The second handling recess 82 is longitudinally aligned to the handling recess 14. The second handling recess 82 and first handling recess 14 may each be used by opposed digits of a user when gripping an injection device 4 accommodated in the channel 6 as will be discussed. The disclosure also includes handling recesses that are not complementary, including differing geometry and longitudinal alignment.

Referring to FIGS. 3 and 6, the first longitudinal wall 58 and second longitudinal wall 10 comprise respective opposed indentations 66, 68 adapted for gripping of the packaging 2. Said adaption comprises a gripping wall 70 arranged with a local depth that extends in the global lateral W direction. The gripping walls 70 may be separated by 4-12 mm or other suitable distance. The gripping wall is dimensioned to fit a digit of a user, e.g., a length in the longitudinal direction L of 2-4 cm an adjoining semi-circular section arranged distal the top adjoining wall 64. Such an arrangement provides a narrowing portion, which may be more convenient to grip then portions of the walls 10, 58 without the indentations, e.g., the narrowing portion enables a greater lateral force to be applied by opposed digits. The indentations extend in the global depth direction from the top adjoining wall 64. Such an arrangement may reduce air locking of stacked packaging since the indentation provides a conduit for pressure relief that extends from the top adjoining wall 64 to a particular depth.

In a variant embodiment, which is not illustrated, the indentations may have other arrangements, including discrete from the adjoining wall 64 and/or with an alternatively profiled gripping wall. In embodiments packaging 2 comprising indentations 64, 66 that are formed without the previously described positioning rib 22 and/or handling recess 14.

The indentations 66, 68 may aid in separating like packaging 2 stacked in the depth direction. The stack may be supplied in an open topped container wherein only the planform of the packaging is user accessible.

Figure 8:
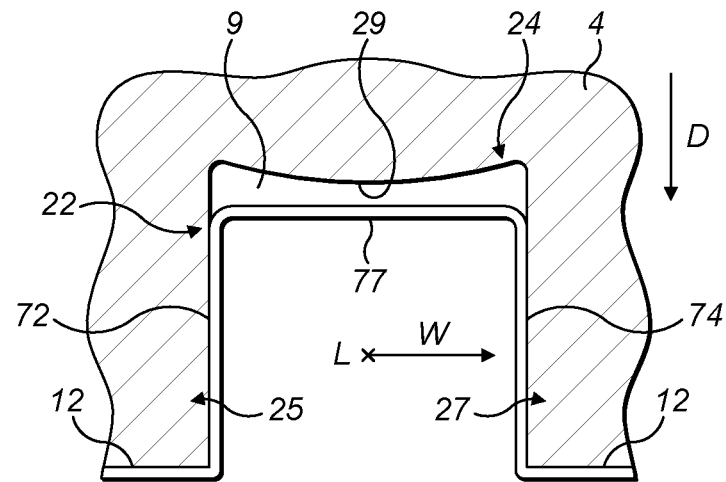
FIG. 8 is a front sectional view showing an embodiment positioning rib of the packaging accommodated in an embodiment positioning recess of an embodiment injection device.

Referring to FIG. 8, the positioning rib 22 has a generally U-shaped cross-section. The lateral position of the rib is central in the channel 6, although the disclosure also includes an eccentric lateral arrangement. The positioning rib 22 includes a first longitudinal wall 72 and a second longitudinal wall 74 interposed by an adjoining top wall 77. The first longitudinal wall 72 and the second longitudinal wall 74 adjoin the base wall 12 of the channel 6.

The first longitudinal wall 72 and a second longitudinal wall 74 are aligned in the depth direction D. In a variant embodiment, which is not illustrated, the first longitudinal wall and the second longitudinal wall of the positioning rib extend along inclined planes (e.g., with a 5-20° incline relative to the depth direction) that intersect at an apex truncated by the adjoining top wall. Such tapering of the positioning rib 22 may facilitate easier locating with the positioning recess 24 and subsequent insertion. The first longitudinal wall 72 and a second longitudinal wall 74 are generally planar, although alternative configurations are included in the disclosure, including curved.

A round adjoins the top wall 77 with the first longitudinal wall 72 and the second longitudinal wall 74. The round may have a radius of 1-3 mm or other suitable amount. Compared to an embodiment (which is also included in the disclosure) with straight edged adjoining walls, embodiments with a round may reduce air locking when the positioning rib 22 is accommodated in the positioning recess 24 of the injection device 4. The round may aid in guiding the rib into the recess during insertion of the injection device 4 into the channel 6. In embodiments the edge is alternatively profiled, including chamfered.

A round adjoins the base wall 12 of the channel 6 and the positioning rib 22. The round may have a radius of 1-3 mm or other suitable amount. The round may reduce air locking when the positioning rib 22 is accommodated in the positioning recess 24 of the injection device 4. The round may increase flexural rigidity of the rib 22 compared to an embodiment (which is also included in the disclosure) with straight edged adjoining walls. In embodiments the edge is alternatively profiled, including chamfered.

Figure 4:
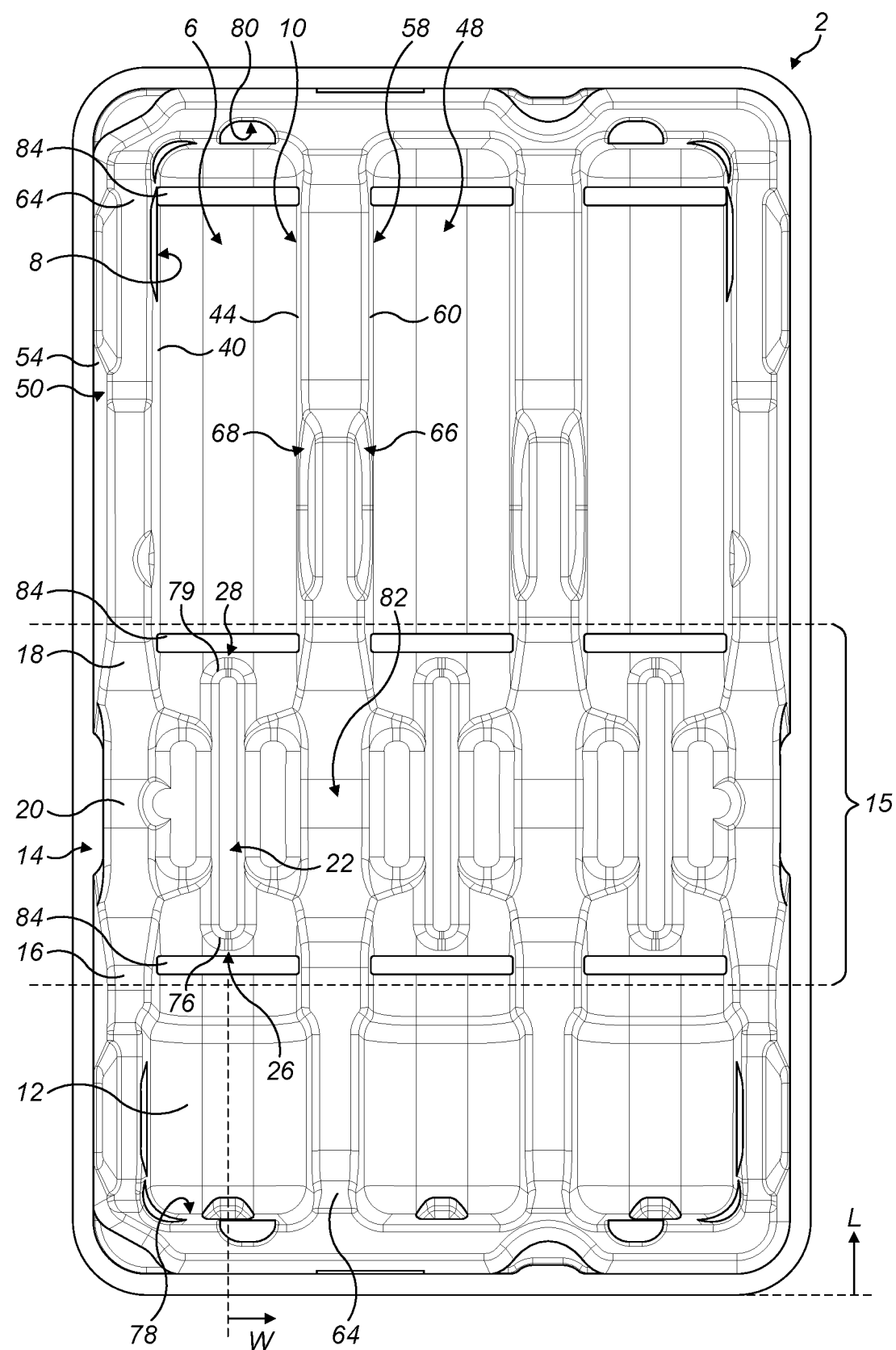
FIG. 4 is a plan view showing a planform of embodiment packaging.

Referring to FIG. 4, the positioning rib 22 includes, arranged at the respective first rib end 26 and second rib end 28 a proximal lateral wall 76 and a distal lateral wall 79. The proximal lateral wall 76 and a distal lateral wall 79 may be similarly configured as for the adjacent first longitudinal wall 72 and a second longitudinal wall 74 in terms of orientation in the depth direction and connection with adjoining edges and optional taper. The proximal lateral wall 76 and distal lateral wall 79 are generally planar, although alternative configurations are included in the disclosure, including curved, including by a full round.

Referring to FIG. 8, the adjoining top wall 77 of the positioning rib 22 is generally planar in the lateral direction W. The base wall 29 of the positioning recess 24 is convex in the lateral direction W. The positioning recess 24 and positioning rib 22 are thus adapted to form a laterally extending concave shaped gap 9 between the top wall 77 of the positioning rib 22 and the base wall 29 of the positioning recess 24 when in an arrangement with the positioning recess 24 accommodating the positioning rib 22.

Figure 9:
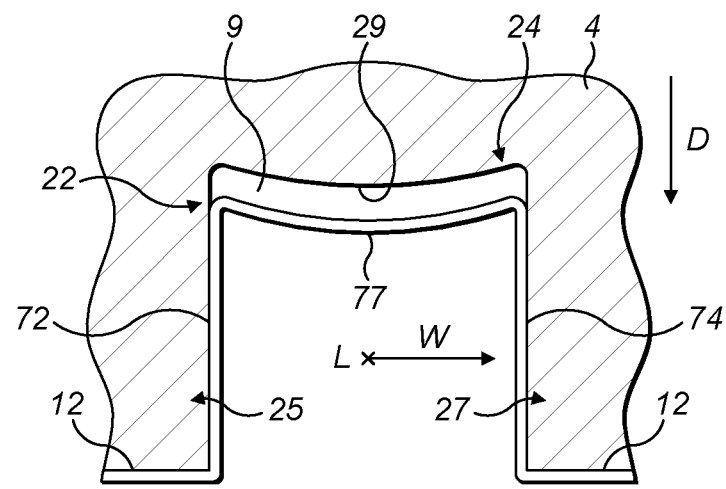
FIG. 9 is a front sectional view showing an embodiment positioning rib of the packaging accommodated in an embodiment positioning recess of an embodiment injection device.

Referring to FIG. 9, the adjoining top wall 77 of the positioning rib 22 is convex in the lateral direction W. The base wall 29 of the positioning recess 24 is convex in the lateral direction W. The positioning recess 24 and positioning rib 22 are thus adapted to form a laterally extending convex shaped gap 9 between the top wall 77 of the positioning rib 22 and the base wall 29 of the positioning recess 24 when in an arrangement with the positioning recess 24 accommodating the positioning rib 22.

Figure 10:
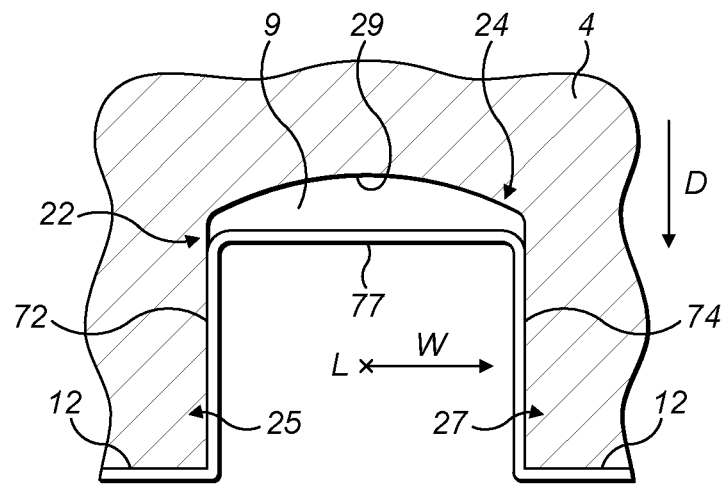
FIG. 10 is a front sectional view showing an embodiment positioning rib of packaging accommodated in an embodiment positioning recess of an embodiment injection device.

Referring to FIG. 10, the adjoining top wall 77 of the positioning rib 22 is generally planar in the lateral direction W. The base wall 29 of the positioning recess 24 is concave in the lateral direction W. The positioning recess 24 and positioning rib 22 are thus adapted to form a laterally extending convex shaped gap 9 between the top wall 77 of the positioning rib 22 and the base wall 29 of the positioning recess 24 when in an arrangement with the positioning recess 24 accommodating the positioning rib 22.

Figure 11:
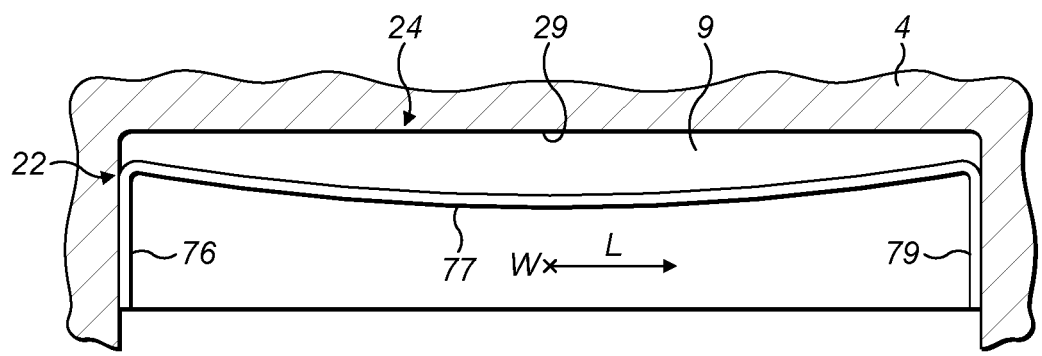
FIG. 11 is a side sectional view showing an embodiment positioning rib of the packaging accommodated in an embodiment positioning recess of an embodiment injection device.

Referring to FIG. 11, the adjoining top wall 77 of the positioning rib 22 is concave in the longitudinal direction L. The base wall 29 of the positioning recess 24 is generally planar in the lateral direction W. The positioning recess 24 and positioning rib 22 are thus adapted to form a longitudinally extending convex shaped gap 9 between the top wall 77 of the positioning rib 22 and the base wall 29 of the positioning recess 24 when in an arrangement with the positioning recess 24 accommodating the positioning rib 22.

The embodiment of FIG. 11 may be combined with any of those associated with FIGS. 8-10. In an embodiment, which is not illustrated, the longitudinally extending convex shape gap may be alternatively formed, including by a longitudinally concave base wall of the positioning recess and a generally planar adjoining top wall of the positioning rib or combinations thereof.

In the preceding embodiments, the lateral concavity may be formed with radii of 2-10 mm, or be alternatively curved, including with a maximum depth from the longitudinal walls 72, 74 of 0.25-2 mm or 0.5-1 mm or 5-20% of the width of the rib. In the preceding embodiments, the longitudinal concavity may be formed with radii of 0.1-0.5 m, or be alternatively curved, including with a maximum depth from the lateral walls 76, 79 of 0.5-3 mm or 0.5-2 mm or 5-20% of the length of the rib. The lateral/longitudinal convexity can be arranged with the equivalent dimensions as for the concavity, which for brevity is not repeated. In general the geometric extent of the concavity/convexity is selected to prevent the rib/recess flexing into each other.

As used herein the term "concave shaped gap" or "convex shaped gap" may refer to a shape of a gap between and formed one or both opposed surfaces of the positioning rib and position rib. The concave/convex shaped gap may extend in the lateral and/or longitudinal directions.

A convex shaped gap 9 may prevent/reduce a portion of the portioning rib 22 flexing into the base wall 29 of the positioning recess 24 of the injection device 4, for instance when in use the top wall 77 of the positioning rib is subject to a compression load. Flexing of the top wall 77 into the base wall 29 may damage the injection device, particularly if the base wall 29 comprises the aforedescribed delivery window, e.g., by marking or otherwise obscuring the peripheral surface.

In the illustrated embodiments the first longitudinal wall 25 and second longitudinal wall 27 of the positioning recess 24 abut the corresponding first longitudinal wall 72 and second longitudinal wall 74 of the positioning rib 22. It will be understood that portions of one or more of the side, end, top and base walls of the positioning rib/recess may be arranged contiguous and/or in abutment to provide the intended positioning of the injection device 4 in the packaging 2.

Referring to FIGS. 4 and 7, the channel 6 includes closing portions comprising a laterally extending proximal end wall 78 and a laterally extending distal end wall 80. The packaging 2 and injection device 4 including the respective positioning rib 22 and positioning recess 24 arranged to locate the injection device 4 in the channel 6 with the distal end 30 and proximal end 32 thereof apart from the respective distal end wall 80 proximal end wall 78. Separating the ends of the injection device from the ends of the channel may reduce risk of damage of the injection device, e.g., a delicate end cap 35 of the proximal end 32 of the injection device 4 is maintained out of abutment with the packaging 2, wherein abutment may effect transfer of load, in case of an impact, to dislodge the endcap. Dislodging of the end cap 35 may cause damage to the subcutaneous delivery member and/or could make the injection device dangerous to handle.

The separation between the proximal end 32 of the injection device 4 and proximal end wall 78 of the packaging 2 may be less than the longitudinal displacement to separate the end cap 35 from the proximal end 32. Separation of the end cap 35 within the packaging 2 may thereby be prevented.

During insertion of the injection device 4 into the packaging 2, the proximal end wall 78 and distal end wall 80 may provide a coarse alignment for the injection device 4 in the channel 6, with fine alignment being subsequently provided by the engagement of the positioning rib 22 and positioning recess 24. In an embodiment the aforedescribed tapering of the proximal end wall 78 and distal end wall 80 of the positioning rib 22 may transition during said insertion (via engagement with the positioning recess 24) the injection device 4 from abutment from one of the proximal or distal end wall 78, 80 to a positioning rib 22 controlled longitudinal location.

In variant embodiments, which are not illustrated, one or both of the proximal end wall 78 and distal end wall 80 may be omitted.

The positioning recess 24 is longitudinally offset with respect to the longitudinal axis of the injection device 4. In a like manner, the positioning rib 22 is longitudinally with respect to the longitudinal axis of the channel 6 of the packaging 2. With such a configuration (compared to the rib and recess being arranged longitudinally centred) the longitudinal orientation of the injection device 4 in the packaging can be controlled, e.g., with the proximal end 32 of the injection device 4 arranged at the intended proximal end of the packaging 2. The arrangement may be further controlled by the inclusion of the proximal end wall 78 and the distal end wall 80 of the channel 2, which can be disposed to block accommodation of the positioning rib 22 in the positioning recess 24 when the proximal end 32 of the injection device 4 is arranged proximal the distal end of the packaging (or the converse). It is to be understood that the disclosure also includes centrally aligned positioning ribs and/or recesses.

The positioning rib 22 and positioning recess 24 can be transitioned between a separated position and an accommodated position (as shown in FIGS. 9 and 10), in which the positioning rib 22 is accommodated in the positioning recess 24 to position the injection device 4 in the channel 6.

In the accommodated position the positioning recess 24 stiffens the packaging 2. Since the geometry of the positioning recess 24 corresponds to the positioning rib 22, the positioning recess 24 can restrain displacement of portions of the accommodated positioning rib 22, said portion can include one or more of the rib: proximal lateral wall 76; distal lateral wall 79; first longitudinal wall 72; second longitudinal wall 74; adjoining top wall 77 (generally in embodiments which do not comprise a adjoining top wall 77).

In the accommodated position the positioning rib 22 and positioning recess 24 may be adapted with various fits. In an embodiment said fit includes a locating fit that does not require an insertion and/or extraction force to transition to/from the accommodated position. Such a fit can be achieved by arranging the positioning rib 22 and positioning recess 24 to have entirely corresponding dimensions and/or the positioning recess 24 to have corresponding dimensions that are greater than those of the positioning rib 22 (or the positioning rib 22 to have corresponding dimensions that are less than those of the positioning rib 24).

In an embodiment said fit includes a force-fit that implements an insertion and/or extraction force to transition to/from the accommodated position. Such a fit can be achieved by arranging the positioning rib 22 to be in an at least partially compressed state when arranged in the accommodated position. The compressed state can be achieved by dimensioning the positioning recess 24 to be smaller than the positioning rib 22, which may include forming part or all of the longitudinal length and/or lateral width of the positioning recess 24 to be less (e.g., by 1-5%) than the corresponding dimension of the positioning rib 22. The compressed state can be achieved by forming the positioning rib 22 to be displaceable in the accommodated position, including via elastic and/or plastic material deformation.

In like embodiments the force-fit is achieved by arranging the positioning recess 24 to be in an at least partially expanded state when arranged in the accommodated position, which in further embodiments may be combined with the positioning rib 22 in the compressed state.

In embodiments a force-fit is achieved by arranging the positioning rib 22 and positioning recess 24 to have entirely corresponding dimensions whereby a material friction coefficient provides the extraction/insertion force.

In an embodiment the force-fit includes an extraction force, to transition from the accommodated position to the separated position, less than a weight of the packaging 2. In an embodiment the mass of the packaging may be 100 grams, wherein the extraction force is less than 1 Newton. It will be understood that the force may vary depending on the configuration (and thus the mass) of the packaging 2, e.g., it can be less than 0.5, 1.5 or 2 Newton. With such an arrangement the packaging 2 may remain in abutment with an abutment surface (e.g., a table) when the device 4 is extracted from the channel 6, and thus the positioning rib 22 retracted from the positioning recess 24.

In embodiments: the positioning rib 22 has a nominal longitudinal length of up to 1.5 or 1 or 0.5% less than that of that of the positioning recess 24; the positioning rib 22 has a nominal lateral width of up to 4 or 6 or 8% less than that of that of the positioning recess 24.

In embodiments: the positioning rib 22 has a nominal longitudinal length of 38.6 mm and a nominal lateral width of 5.2 mm; and the positioning recess 24 has a nominal longitudinal length of 38.8 mm and a nominal lateral width of 5.4 mm. In embodiments each of the described dimensions may be ±1% or 5% or 10%. The total distance between the positioning rib 22 and positioning recess 24 in the lateral and longitudinal direction may be 0.2 mm±1% or 5% or 10%.

In embodiments the positioning rib 22 is operatively arranged for stiffening of the handling recess 14, e.g., the positioning rib 22 increases the resistance of the packaging to bending moment applied about a laterally extending axis. The handling recess 14 may be stiffened in terms of a flexural rigidity extending longitudinally along said recess. The positioning rib 22 thus compensates for the loss of stiffness due to the formation of the handling recess 14 through the associated walls. Suitable arrangements of the positioning rib 22 may include the geometric configuration of the rib (e.g., one or more of the length, depth, width) specifically selected for stiffening. Said arraignment may include the positioning of the rib (e.g., aligned to the handling recess 14).

In embodiments the positioning rib 22 has a depth 'd' of about 25% or 20-30% of a depth 'j' of the recess 14 (i.e., the nominal depth of the adjoining wall 20 from the top adjoining wall 64 of the handling recess 14). In embodiments the positioning rib 22 has a longitudinal length T about 24% or 20-30% or 15-35% of a longitudinal length of the channel 6. In embodiments the positioning rib 22 has a lateral width 'w' of about 3% or 2-4% of a longitudinal length of the channel 6. In embodiments the positioning rib 22 has a lateral width W of about 20% or 15-25% of a lateral width of the channel 6. In embodiments j is about 8% or 6-10% or 4-15% or 2-20% of the product of w and $d^3$.

Figure 12:
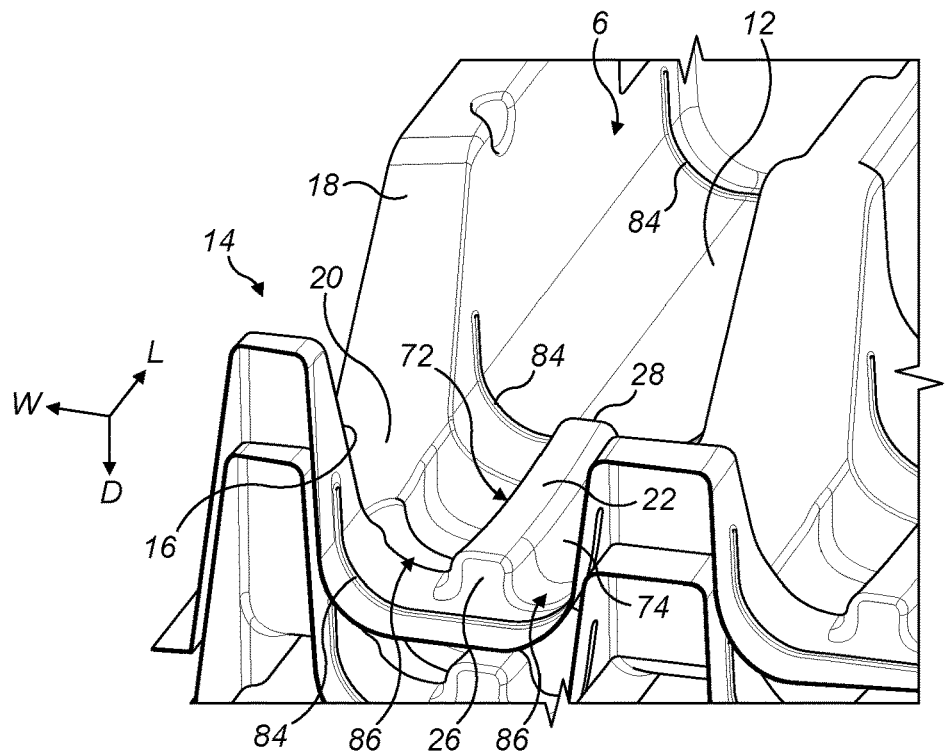
FIGS. 12 and 13 are perspective views showing a portion of the embodiment packaging of FIG. 4.

Referring to FIGS. 4, 7 and 12 the channel 6 includes laterally extending abutment ribs 84, 85. The abutment ribs 84, 85 are arranged to abut the injection device 4 accommodated in the channel 6. The abutment ribs 84, 85 include curved protrusions that protrude into the channel 6. The abutment ribs 84, 85 may stiffen sections of the channel. The abutment ribs 84 are arranged within the longitudinal field 15 of the lateral walls 16, 18 of the handling recess 14. The abutment rib 85 is arranged at the distal end of the channel 6. The abutment ribs 84, 85 are formed of a single protrusion.

The abutment ribs 84, 85 may prevent/reduce lateral movement of the injection device 4 accommodated in the channel 6. The abutment ribs 84, 85 may control portions of the body 29 of the device 4 abutted by the packaging. The portion abutted may receive wear due to friction, thus the abutment ribs 84, 85 may localise such wear. In an example, the wear may be directed away from the label 52 so as to avoid obscuring instructions thereof.

In variant embodiments, which are not illustrated, the abutment ribs may be alternatively arranged, e.g., the abutment ribs may be protrude with other suitable shapes including V-shaped or Square-shaped. The abutment ribs may be formed of multiple adjacent protrusions. The abutment ribs may be alternatively located, including at the proximal end of the channel.

Figure 13:
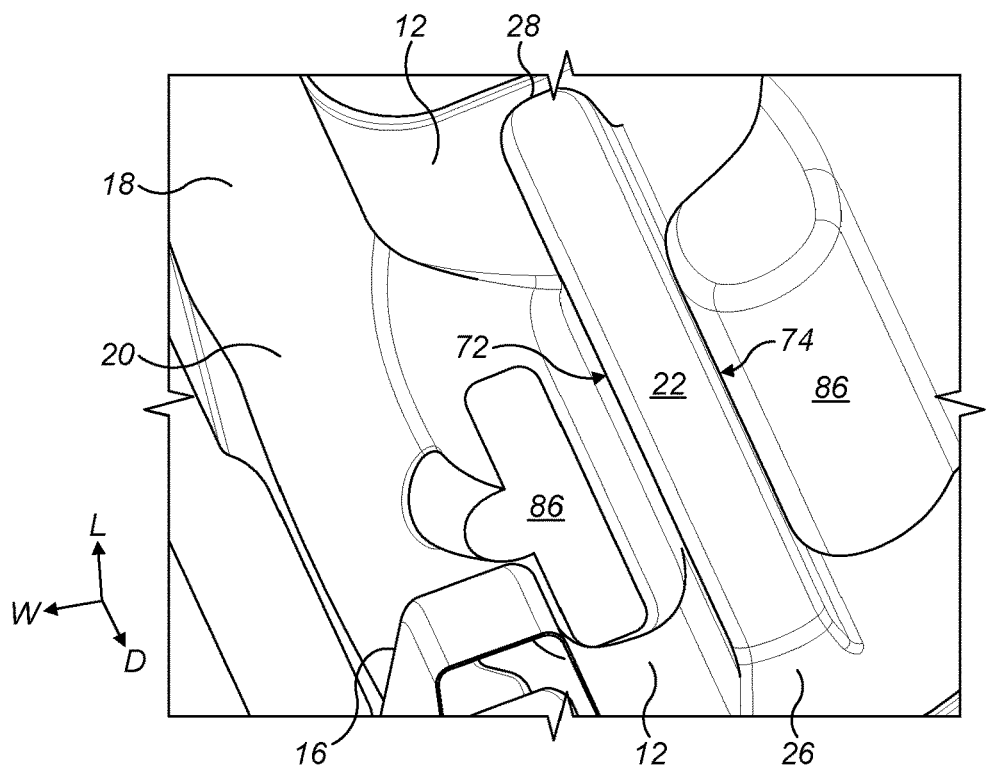

Referring to FIGS. 12 and 13, the channel 6 includes longitudinally extending cut-outs 86 arranged adjacent each longitudinal wall 72, 74 of the positioning rib 22. The cut-outs 86 project as cavities from the base 12 of the channel in the depth direction D, hence in the opposed direction to the positioning rib 22. The cut-outs 86 may enhance stiffness proximal the handling recess 14. The cut-outs 86 may facilitate more convenient gripping of an injection device 4 accommodated in the channel 6 by enabling a user to partially insert their digits into the cut-outs when gripping the device 4.

Figure 14:
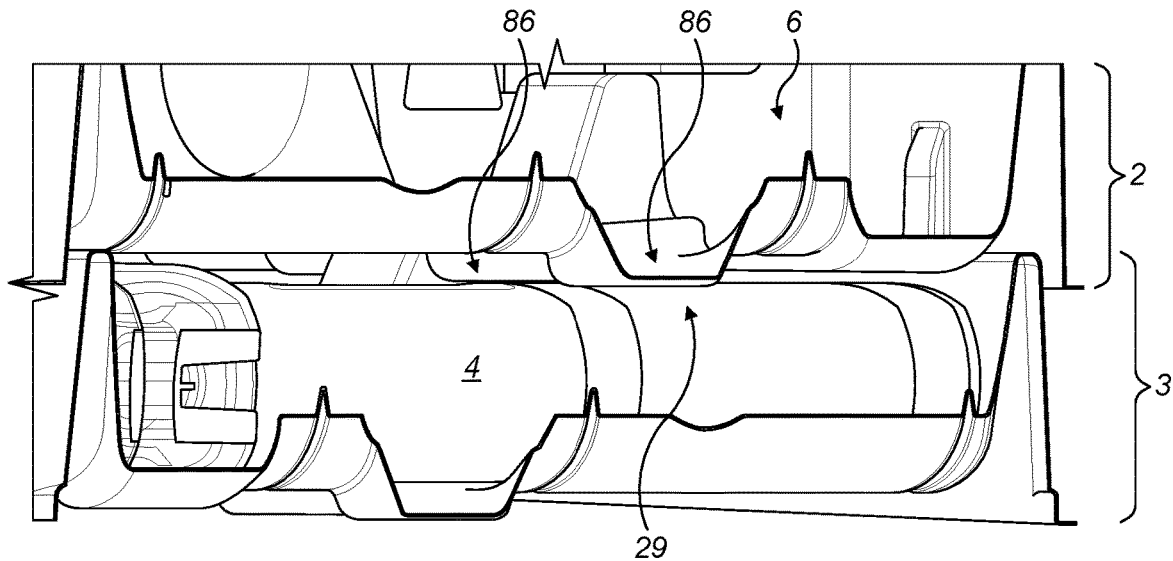
FIG. 14 is a perspective cut-away view showing abutment between stacked packaging of the embodiment packaging of FIG. 4 and an injection device accommodated in the packaging.

Referring to FIG. 14, the cut-outs 86 may protrude to abut the body 29 of an injection device 4 accommodated in adjacent like packaging 3, which is stacked in the depth direction beneath the packaging 2. The cut-outs 86 may restrain the abutted injection device 4.

Figure 15:
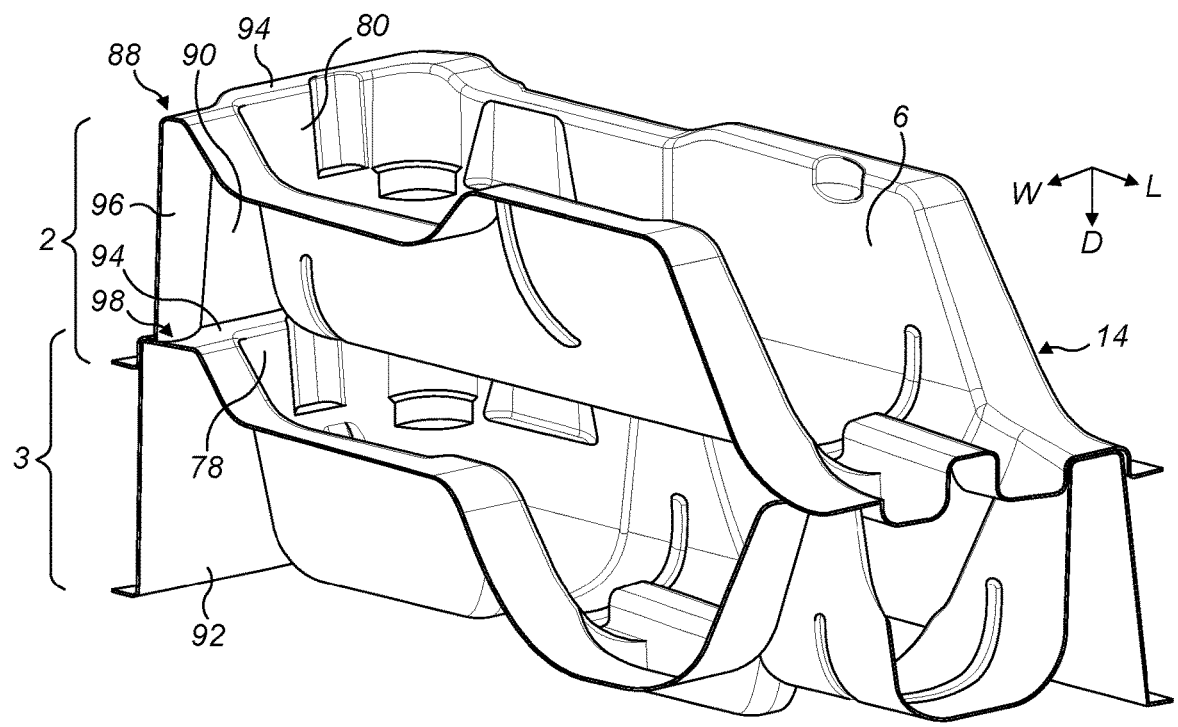
FIG. 15 is a perspective cut away view showing stacked packaging extending in a longitudinal direction, the packaging of the embodiment packaging of FIG. 4.
Figure 16:
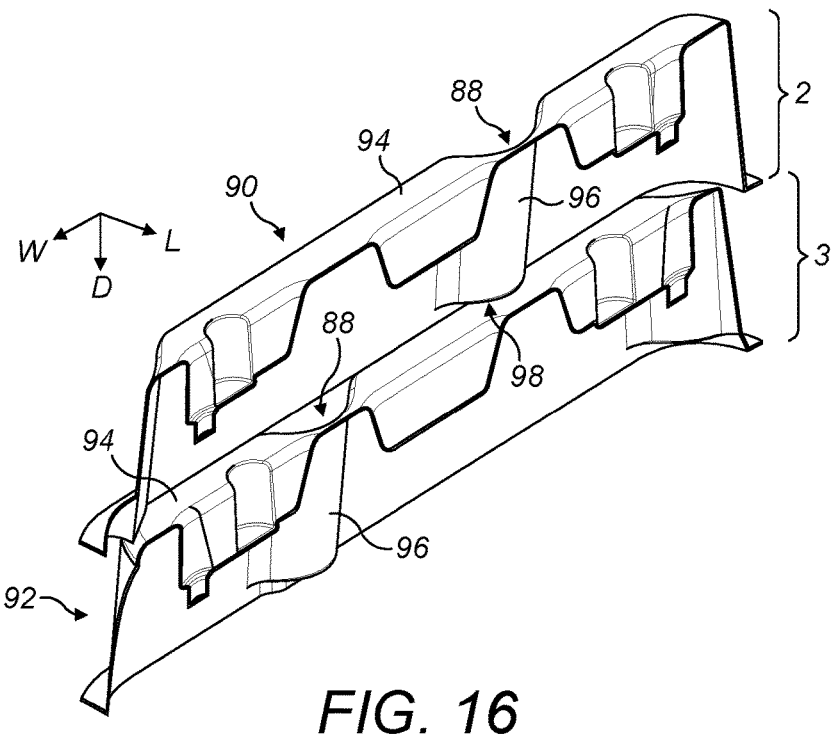
FIG. 16 is a perspective cut away view showing a peripheral lateral wall of stacked packaging, the packaging of the embodiment packaging of FIG. 4.
Figure 17:
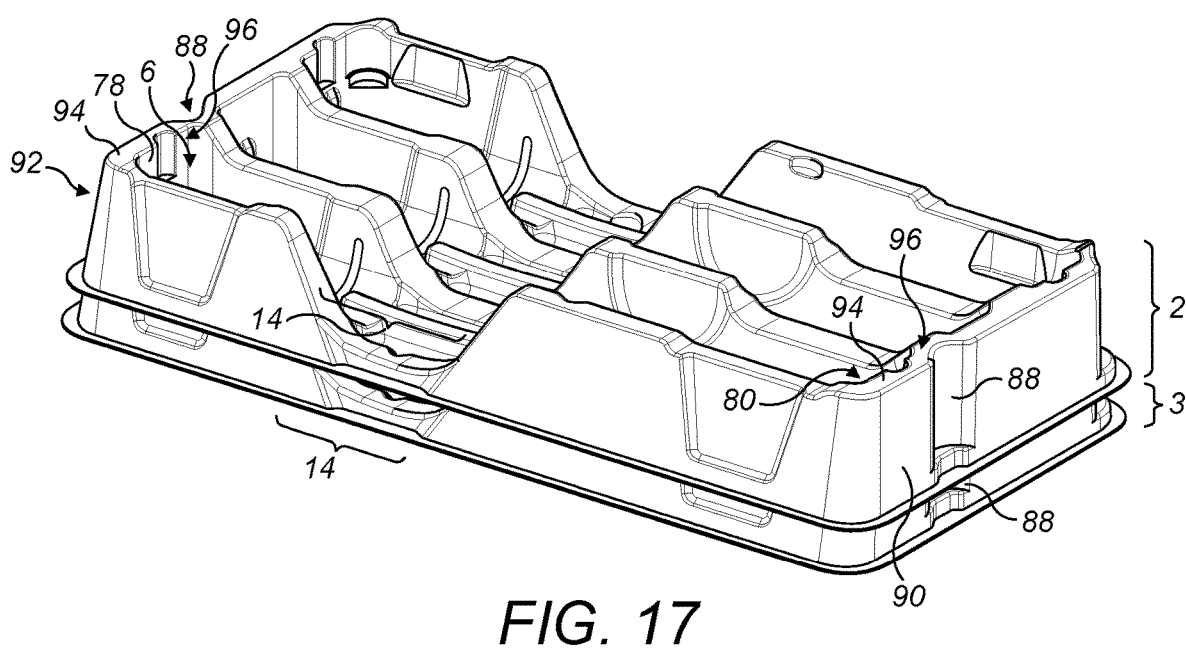
FIG. 17 is a perspective view showing stacked packaging, the packaging of the embodiment packaging of FIG. 4.

Referring to FIGS. 14-17, the packaging may be adapted to provide various stacking configurations. Referring to FIG. 17, the packaging 2 is adapted to enable insertion into corresponding adjacent packaging 3. The insertion is to a first depth with the packaging 2, 3 both correspondingly arranged in a first position. The first depth comprises a substantial portion (e.g., at least 60-90%) of the depth of the packaging such that packaging without an injection device accommodated therein can be conveniently stacked and stowed.

The adaptation may comprise a general correspondence of adjacent portions of the packaging 2, 3 including by tapering and rounding as discussed previously. Referring to FIG. 17, the adaptation includes grooves 88 arranged through an exterior face of a distal 90 and proximal 92 peripheral lateral wall. Adjoining walls 94 adjoin the proximal peripheral lateral wall 92 and proximal end wall 78 of the channel 6, and the distal peripheral lateral wall 90 and distal end wall 80 of the channel 6. The grooves 88 form corresponding protrusions 96 on opposed interior faces of the peripheral lateral walls 90, 92. A protrusion 96 of the packaging 2 is insertable into the groove 88 of packaging 3 for said stacking.

The grooves 88 extend in the depth direction to proximal a base of the peripheral walls 90, 92. The grooves have a generally curved cross section, which may aid insertion of a corresponding protrusion.

Referring to FIGS. 15 and 16, the packaging 2 is adapted to enable insertion into corresponding adjacent packaging 3 to a second depth, which is less that the first depth, with the packaging 2, 3 arranged in a second position. In the second position the packaging 3 is rotated about the depth axis by 180° relative the packaging 2. In this position a base 98 of the groove 88 of packaging 2 abuts the adjoining walls 94 of packaging 3 to provide a stable abutment. The abutment may prevent excessive contact between an injection device 4 arranged in the packaging 3 and the stacked packaging 2.

The abutment of the base 98 of the groove 88 of packaging 2 with the adjoining wall 94 of packaging 3 with the packaging 2, 3 arranged in the second position and the insertion of the protrusion 96 of packaging 2 in to groove 88 of packaging 3 with the packaging 2, 3 arranged in the first position can be achieved by eccentrically arranging the grooves 88 with respect to width. In the illustrated embodiment the eccentric arrangement comprises the groove 88 arranged proximal an end channel 6, rather than at the centre along the peripheral wall.

In embodiments, which are not illustrated, the grooves may be alternatively and/or additionally arranged, e.g., including though the peripheral longitudinal wall 50 or the channel 6. Reference to grooves can include formation on the interior or exterior face of a peripheral wall, or other wall. The grooves may be alternatively shaped, e.g., including a linear rather that curved cross section.

In variant embodiments, the positioning rib 22 may be formed of more than one protrusion. An example includes a separate first protrusion and second protrusion arranged at the respective first rib end 26 and at the second rib end 28. Reference to a positioning rib herein may therefore refer to a rib formed of one or a plurality of separated protrusions.

The packaging may be formed by thermoforming, vacuum forming, casting or other forming process known to the skilled person. Typically the single plastic sheet in planar form is thermoformed to the desired profile via a mould and other associated equipment known to the skilled person. Suitable materials for the plastic sheet include polystyrene. Suitable gauges for the plastic sheet prior to forming include 0.6 mm.

An embodiment method of stowing embodiment injection device 4 (or a like configured injection device training device) in packaging 2 as disclosed herein may include arranging said the injection device 4 in an aligned position with the first recess end 34 and the second end 36 of the positioning recess 24 and/or 38 thereof longitudinally aligned with the respective first lateral wall 16 and the second lateral wall 18 handling recess 14. The user may displace the injection device 4 arranged in said aligned position in the depth direction to insert it into the channel 6, which may include the positioning rib 22 and positioning recess 24 or 38 arranged in the accommodated position.

Referring to an embodiment comprising: a second positioning recess 38 arranged opposed and longitudinally aligned to the positioning recess 24; and the associated first rib 26 ends and second rib ends 28 arranged aligned in the longitudinal direction to the respective first lateral wall 16 and second lateral 18 wall of the handling recess 14. A user may in the aligned position align the first rib 26 end and second rib end 28 of the positioning recess 38, with said recess 38 arranged visible from above the packaging, with the first lateral wall 16 and second lateral 18 wall of the recess 14, which therefore ensures longitudinal alignment of the positioning rib 22 and positioning recess 24. Thus the arrangement of the positioning recess 38 and handling recess 14 may be used as a longitudinal guide during insertion.

In an embodiment method of extracting an injection device 4 (or a like configured injection device training device) stowed in packaging 2 as disclosed herein may include inserting a digit (not shown) of a user into the handling recess 14. The insertion may include movement of said digit in the depth and/or lateral direction. The method may include gripping said device and extracting it from the channel 6. Extracting the device 4 from the channel 6 may include transitioning the positioning rib 22 and positioning recess 24 from the accommodated position to the separated position, including by displacement of the injection device in the opposed depth direction. Gripping the device 4 may include the application of a force in the lateral direction to the device by said digit arranged in the handling recess 14. In embodiments comprising the handling recess 14 and a complementary second handling recess 82, gripping the device 4 may include the application of opposed lateral force by opposed digits, each arranged in one of the recesses 14, 82.

From the described embodiments it will be understood that the packaging 2 may enable convenient extraction of the injection device 4. The handling recess 14 conveniently enables a user to access the channel 6 for gripping, by opposed digits, of the accommodated injection device 4. The injection device may by extracted without complex movements, such as rotation of the device and/or a hand of the user. It will thus be understood that the packaging is suited for use by users with a disorder that effects dexterity. Thus the injection device 4 preferably includes a medicament for treatment or prevention of such an illness.

To close the channel 6, 48 of the packaging 2 and/or secure the injection device 4 therein various arraignments (not shown) may be provided, which may be referred to as a lid.

In an embodiment a tear away or break through lid may be provided as medical blister type packaging. A lidding film may provide a peel-open feature that can be peeled open using two-hands, including by a knuckle-roll-peel technique. The lidding film can be made from plastic, aluminium, medical grade papers, or other suitable material. A lidding film of a blister pack may be permeable to gas porous to allow sterilization but not permeable to microorganisms. A presently available example plastic material is Tyvek® by DuPoint™. The lidding film may be made from a completely non-permeable or non-breathable film. In instances where a non-breathable film is used, sterilization can be via an electron beam or similar.

In an embodiment, the lid may comprise a thick plastic sheet, which may correspond to that forming the channel 6, 48, thus providing a medical tray or medical clamshell type packaging.

Embodiments are also provided according to the following clauses:

Clause 1. Packaging 2 for an injection device 4, the packaging may include a channel 6 extending longitudinally to accommodate the injection device, the channel including a longitudinal wall 8 adjoining a base wall 12; a handling recess 14 extending laterally and formed through the longitudinal wall 8, a positioning rib 22 extending longitudinally and protruding from the base wall into or away from the channel for insertion into a positioning recess 24 of the injection device, the positioning rib arranged offset laterally from the recess. The positioning rib may and extend in and/or outside of a longitudinal field 15 defined by the handling recess.

Clause 2. The packaging of clause 1 or another embodiment disclosed herein, wherein the handling recess 14 including a first lateral wall 16 and a second lateral wall 18 interposed by an adjoining wall 20. The positioning rib 22 may include a first rib end 26 and second rib end 28. The first rib end may be arranged: aligned longitudinally to the first lateral wall; arranged outside of the longitudinal field 15 defined by the handling recess; arranged within of the longitudinal field 15 defined by the handling recess. The second rib end may be arranged: aligned longitudinally to the second lateral wall; arranged outside of the longitudinal field 15 defined by the handling recess; arranged within of the longitudinal field 15 defined by the handling recess. Any combination of the preceding first and second rib end arrangements is included within the disclosure. The entire rib may extend outside of or within the longitudinal field 15 defined by the handling recess.

Clause 3. The packaging of either of clauses 1 or 2 or another embodiment disclosed herein, wherein the positioning rib 22 is formed as a single protrusion.

Clause 4. The packaging of any of clauses 2-3 or another embodiment disclosed herein, wherein the first lateral wall 16 and the second lateral wall 18 of the handling recess 14 extend along inclined planes 19 that intersect at an apex 21 and are truncated by the by the adjoining wall 20.

Clause 5. The packaging of any preceding clause or another embodiment disclosed herein, wherein the positioning rib 22 has a lateral width 'w' a depth 'd' and the handling recess has a depth 'j', wherein j is 4-15% of the product of w and $d^3$.

Clause 6. The packaging of any preceding clause or another embodiment disclosed herein, wherein the positioning rib 22 includes a first longitudinal wall 72 and a second longitudinal wall 74 interposed by an adjoining top wall 77, the first longitudinal wall 72 and the second longitudinal wall 74 adjoining the base wall 12 of the channel 2.

Clause 7. The packaging of clause 6 or another embodiment disclosed herein, wherein a top wall 77 of the positioning rib 22 is concave in the lateral direction.

Clause 8. The packaging of either clause 6 or clause 7 or another embodiment disclosed herein, wherein a round adjoins the adjoining top wall (77) with the first longitudinal wall (72) and the second longitudinal wall (74).

Clause 9. The packaging of any of clauses 6-8 or another embodiment disclosed herein, wherein a round adjoins the base wall 12 of the channel 6 and the positioning rib 22.

Clause 10. The packaging of any preceding clause or another embodiment disclosed herein, wherein the positioning rib 22 is dimensioned with: a longitudinal length of 38.6 mm and a lateral width of 5.2 mm±5, or 10% or 20%.

Clause 11. The packaging of clause 2 or another embodiment disclosed herein, wherein the base wall 12 of the channel 6 is arranged with a greater depth than the adjoining wall 20 of the handling recess 14.

Clause 12. The packaging of any preceding clause or another embodiment disclosed herein, wherein a further longitudinal wall 50 extends contiguous the longitudinal wall 8 of the channel 12, the handling recess 14 formed through the further longitudinal wall 50.

Clause 13. The packaging of clause 12 or another embodiment disclosed herein, wherein the further longitudinal wall 50 and longitudinal wall 8, comprise opposed indentations 66, 68 adapted for gripping of the packaging, the indentations extending in a depth direction from a top adjoining wall 64, that interposes and adjoins the further longitudinal wall 50 and longitudinal wall 8.

Clause 14. The packaging of any preceding clause or another embodiment disclosed herein, wherein a top wall 77 of the positioning rib 22 is concave shaped and/or another shape suitable for preventing the top wall flexing into an adjacent surface of the positioning recess of the injection device. The concave shape may extend in the lateral and/or longitudinal direction. The concave shape may extend generally between outer walls (e.g., lateral or longitudinal wall that defines the rib). The concave shape may be generally curved and/or partially linear.

Clause 15. The packaging of any preceding clause or another embodiment disclosed herein, wherein the base wall of the channel includes longitudinally extending cut-outs 86 arranged on one or both sides of the positioning rib 22. The cut-outs may protrude in an opposed direction to the positioning rib 22.

Clause 16. The packaging of any preceding clause or another embodiment disclosed herein, wherein the channel 6 includes laterally extending abutment ribs 84. The abutment ribs may be arranged proximal the ends of the positioning rib 22.

Clause 17. Packaging 2 for an injection device 4, the packaging may include the packaging of any preceding clause or another embodiment disclosed herein. The packaging may include: a channel 6 extending longitudinally to accommodate the injection device, the channel including a longitudinal wall 8 adjoining a base wall 12; a handling recess 14 extending laterally and formed through the longitudinal wall 8, a positioning rib 22 extending longitudinally and protruding from the base wall into the channel for insertion into a positioning recess 24 of the injection device, the positioning rib arranged offset laterally from the handling recess and arranged longitudinally in the channel to stiffen the handling recess, including a flexural rigidity longitudinally along the handling recess.

Clause 18. Packaging 2 for an injection device 4. The packaging may include the packaging of any preceding clause or another embodiment disclosed herein. The packaging comprising: a channel 6 extending longitudinally to accommodate the injection device, the channel including a longitudinal wall 8 adjoining a base wall 12; a positioning rib 22 extending longitudinally and protruding from the base wall into the channel for insertion into a positioning recess 24 of the injection device, wherein a top wall 77 of the positioning rib 22 is concave shaped.

Clause 19. A system comprising the packaging 2 of any preceding clause or another embodiment disclosed herein, and an injection device 4, or injection device training device, for accommodating in the channel 6 of the packaging, wherein said device comprises a positioning recess 24 to accommodate the positioning rib 22.

Clause 20. The system of clause 19 or another embodiment disclosed herein, wherein, with the positioning recess 24 accommodating the positioning rib 22, the positioning recess 24 of the device 4 and the adjoining top wall 77 of the positioning rib 22 are adapted to form a convex shaped gap between the adjoining top wall of the positioning rib and an opposed surface 29 of the positioning recess 24. The convex shaped gap may be in the lateral or longitudinal direction.

Clause 21. The system of either clause 19 or clause 20 or another embodiment disclosed herein, wherein the positioning recess 24 of the device 4 and positioning rib 22 of the packaging 2 are arranged to locate the device in the channel 6 with: a distal end 30 of the device arranged apart from a distal end wall 80 of the channel 6; and/or a proximal end 32 of the device arranged apart from a proximal end wall 78 of the channel 6.

Clause 22. The system of any of clauses 19-20 or another embodiment disclosed herein, wherein the positioning recess 24 of the device 4 are arranged to prevent accommodation of the injection device 4 in the channel 6 with: a distal end 30 of the device arranged proximal the proximal end wall 78 of the channel 6; and/or a proximal end 32 of the device arranged proximal the distal end wall 80 of the channel 6.

Clause 23. The system of any of clauses 19-21 or another embodiment disclosed herein, wherein the positioning recess 24 of the device 4 is arranged to be contiguous and/or in abutment with an accommodated positioning rib 24 of the packaging 2.

Clause 24. The system of any of clauses 19-23 or another embodiment disclosed herein, wherein the device 4 comprises a further positioning recess 38 arranged longitudinally aligned and opposed positioning recess 24.

Clause 25. The system of any of clauses 19-24 or another embodiment disclosed herein, wherein injection device 4 comprises a label 52, the positioning rib 22, positioning recess 24 and label 52 arranged with the label visible from a planform of the packaging (e.g. when viewed in the depth direction from above the packaging), with the positioning rib 22 accommodated in the positioning recess 24 (e.g. with the injection device accommodated in the channel).

Clause 26. The system of any of clauses 19-25 or another embodiment disclosed herein, wherein injection device 4 comprises a label 52, wherein the label 52 is longitudinally offset from the positioning rib 22.

Clause 27. The system of any of clauses 19-26 or another embodiment disclosed herein, wherein the positioning rib 22 and positioning recess 24 are adapted with a force-fit connection, wherein the force-fit connection includes an extraction force less than a weight of the packaging 2.

Clause 28. A pre-packaged injection device 4, or injection device training device, arranged with a positioning recess 24 thereof accommodating a positioning rib 22 of the packaging 2 of any of clauses 1-25 or another embodiment disclosed herein.

Clause 29. The system of any of clauses 19-27 or the pre-packaged injection device of clause 26 or another embodiment disclosed herein, wherein the injection device comprises a medicament as disclosed herein.

Clause 30. The system of any of clauses 19-27 or 29 or the pre-packaged injection device clause 26 or another embodiment disclosed herein, wherein the injection device is for use in the treatment or prevention of a disorder as disclosed herein.

Clause 31. Use of the packaging 2 of any of clauses 1-19 or another embodiment disclosed herein, for accommodating an injection device or an injection device training device.

Clause 32. Use of an injection device 4 for accommodating and restraining the positioning rib 22 of the packaging 2 of any of clauses 1-19 or another embodiment disclosed herein, Clause 33. The injection device of any preceding clause including a medicament as disclosed herein.

Clause 34. An injection device comprising a positioning recess 24 adapted to accommodate the positioning rib 22 of the packaging 2 of any of clauses 1-19 or another embodiment disclosed herein. The injection device may include a medicament as disclosed herein, e.g., arranged in a container thereof.

Clause 33. A method of stowing an injection device 4 or injection device training device, in packaging 2. The packaging may be according to any of clauses 1-32 or another embodiment as disclosed herein, the method may include arranging said device with a positioning recess 24, 38 thereof arranged within a longitudinal field 15 defined by a handling recess 14 of the packaging 2, the handling recess 14 extending laterally an arranged through a longitudinal wall 6, the longitudinal wall 6 forming a longitudinally extending channel 4 to accommodate the injection device, inserting the aligned device into the channel.

Clause 34. The method of clause 34 or another embodiment disclosed herein, including inserting a positioning rib 22 of the channel 6 of the packaging 2 into a positioning recess 24 of the device, the positioning rib arranged within a longitudinal field of the handling channel 14.

Clause 35. A method of stiffening injection device packaging 2. The packaging may be according to any of clauses 1-34 or another embodiment as disclosed herein, the method may include accommodating a positioning rib 22 of packaging within a positioning recess 24 of an injection device 4, wherein the positioning recess cooperates with the positioning rib to support the positioning rib, the positioning rib arranged longitudinally in a channel 6 to accommodate the injection device, the positioning rib to increase a flexural rigidity longitudinally along a laterally extending handling recess.

Clause 36. A method of extracting an injection device 4, or injection device training device, stowed in packaging 2. The packaging may be according to any of clauses 1-34 or another embodiment as disclosed herein, the method may include inserting a digit of a user into a laterally extending handling recess 8, the recess arranged through a longitudinal wall 8, the longitudinal wall 8 forming a longitudinally extending channel 6 to accommodate said device, the channel comprising a longitudinally extending rib 22 operatively arranged to stiffen the handling recess. The method may include gripping said device with the digit and extracting it from the channel.

Clause 37. Packaging 2 for an injection device 4, the packaging may include the packaging of any preceding clause or another embodiment disclosed herein. The packaging may be arranged to be insertable into corresponding packaging to a first depth, wherein the packaging and corresponding packaging have a first orientation, which comprises corresponding orientation. The first orientation may include the corresponding packaging with a distal end thereof arranged proximal a distal end of the packaging. The packaging may be arranged to be insertable into corresponding packaging to a second depth, wherein the packaging and corresponding packaging have an alternative second orientation. The second orientation may include the corresponding packaging with a distal end thereof arranged proximal a proximal end of the packaging. The packaging may include a groove 88 forming a corresponding protrusion 96 for insertion into a corresponding groove 88 of the corresponding packaging. The protrusion 96 of the packaging may be insertable into the groove of the corresponding packaging in the first orientation. In the second orientation, a base 98 of the groove 88 of the packaging may abut a wall 94 of the corresponding packaging to restrict insertion to the second depth. In the first orientation the base 98 of the groove 88 of the packaging may restrict insertion depth.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

Unless otherwise explicitly stated as incompatible, or the physics or otherwise of the embodiments, example or claims prevent such a combination, the features of the foregoing embodiments and examples, and of the following claims may be integrated together in any suitable arrangement, especially ones where there is a beneficial effect in doing so. This is not limited to only any specified benefit, and instead may arise from an "ex post facto" benefit. This is to say that the combination of features is not limited by the described forms, particularly the form (e.g., numbering) of the example(s), embodiment(s), or dependency of the claim(s). Moreover, this also applies to the phrase "in one embodiment", "according to an embodiment" and the like, which are merely a stylistic form of wording and are not to be construed as limiting the following features to a separate embodiment to all other instances of the same or similar wording. This is to say, a reference to 'an', 'one' or 'some' embodiment(s) may be a reference to any one or more, and/or all embodiments, or combination(s) thereof, disclosed. Also, similarly, the reference to "the" embodiment may not be limited to the immediately preceding embodiment.

Unless otherwise stated, an object which is said to extend in a particular direction is to be construed as having a component of a directional vector that extends in said direction and does on preclude the extension in alternative directions.

The foregoing description of one or more implementations provides illustration and description, but is not intended to be exhaustive or to limit the scope of the invention to the precise form disclosed. Modifications and variations are possible in light of the above teachings or may be acquired from practice of various implementations of the present disclosure.

LIST OF REFERENCES

2 Packaging
  6, 48 Channel
    8, 58 First longitudinal wall
      40, 60 First face
      42, 62 Second face
      66 Indentation
        70 Gripping wall
    10 Second longitudinal wall
      44 First face
      46 Second face
      68 Indentation
        70 Gripping wall
    50 Peripheral longitudinal wall
      54 First face
      56 Second face
    64 Top adjoining wall
  12 Base wall
  22 Positioning rib
    26 First rib end
      76 Proximal lateral wall
    28 Second rib end
      79 Distal lateral wall
    72 First longitudinal wall
    74 Second longitudinal wall
    77 Adjoining top wall
    78 Proximal end wall
    80 Distal end wall
  14, 82 Handling recess
    15 Longitudinal field
    16 First lateral wall
    18 Second lateral wall
    20 Adjoining wall
      23 Reinforcing rib
4 Injection device
  29 Body
    24, 38 Positioning recess
      25 First longitudinal wall
      27 Second longitudinal wall
      29 Base wall
      34 First recess end
        31 Proximal lateral wall
      36 Second recess end
        33 Distal lateral wall
      52 label
  30 Distal end
  32 Proximal end
    35 End cap
  11 Longitudinal axis

The invention claimed is:

1. A kit comprising a packaging and an injection device, wherein the injection device defines a positioning recess, wherein the packaging comprises:
a channel extending longitudinally to accommodate the injection device, the channel including a first longitudinal wall, a second longitudinal wall opposing the first longitudinal wall, and a base wall extending between the first longitudinal wall and the second longitudinal wall;
a first handling recess defined by the first longitudinal wall and a second handling recess defined by the second longitudinal wall; and
a positioning rib protruding from the base wall into the channel for insertion into the positioning recess of the injection device, the positioning rib having a length in the longitudinal direction that is greater than a width in the lateral direction,
wherein a lateral position of the positioning rib is central in the channel and a longitudinal position of the positioning rib is eccentric in the channel.

2. The kit of claim 1, wherein the positioning recess comprises a delivery window for visual feedback of medicament delivery.

3. The kit of claim 1, wherein the injection device has a circular cross section along the longitudinal direction.

4. The kit of claim 1, wherein:
the channel further includes a first lateral wall and a second lateral wall, and
the base wall extends between the first lateral wall and the second lateral wall.

5. The kit of claim 1, wherein the positioning rib is offset longitudinally from the first handling recess or the second handling recess.

6. The kit of claim 1, wherein the first longitudinal wall or the second longitudinal wall comprises a grip for gripping of the packaging.

7. The kit of claim 6, wherein the grip is an indentation extending laterally into the first longitudinal wall or the second longitudinal wall.

8. The kit of claim 1, wherein the positioning rib extends longitudinally outside of the first handling recess or the second handling recess.

9. The kit of claim 1, wherein a top surface of the positioning rib is concave in the lateral direction.

10. The kit of claim 1, wherein the longitudinal length of the positioning rib is 38.6 mm±10% and the lateral width of the positioning rib is 5.2 mm±10%.

11. The kit of claim 1, wherein the injection device comprises a medicament including at least one of glatiramer acetate, adalimumab, an anti-CGRP antibody, reslizumab, a follicle-stimulating hormone, or a substance for use in treatment or prevention of a disorder that affects dexterity of a user.

12. A kit comprising a packaging and an injection device, wherein the injection device defines a positioning recess and comprises a label, wherein the packaging comprises:
- a channel extending longitudinally to accommodate the injection device, the channel including a first longitudinal wall, a second longitudinal wall opposing the first longitudinal wall, and a base wall extending between the first longitudinal wall and the second longitudinal wall;
- a first handling recess defined by the first longitudinal wall and a second handling recess defined by the second longitudinal wall; and
- a positioning rib protruding from the base wall into the channel, the positioning rib having a length in the longitudinal direction that is greater than a width in the lateral direction,
- wherein a lateral position of the positioning rib is central in the channel, and wherein, when the injection device is in the channel, the positioning recess accommodates the positioning rib and the label is visible from a planform of the packaging.

13. The kit of claim 12, wherein the positioning recess comprises a delivery window for visual feedback of medicament delivery.

14. The kit of claim 12, wherein the label is longitudinally offset from the positioning rib.

15. The kit of claim 12, wherein, when the positioning recess accommodates the positioning rib, the positioning recess of the injection device and a top wall of the positioning rib define a convex-shaped gap between the top wall and the positioning recess.

16. The kit of claim 12, wherein the injection device further comprises a further positioning recess longitudinally aligned and circumferentially opposed the positioning recess.

17. The kit of claim 12, wherein the positioning recess accommodates the positioning rib with a force-fit connection having an extraction force less than a weight of the packaging.

18. The kit of claim 12, wherein a longitudinal position of the positioning rib is eccentric in the channel.

19. The kit of claim 12, wherein the first longitudinal wall or the second longitudinal wall comprises a grip for gripping of the packaging.

20. The kit of claim 12, wherein the longitudinal length of the positioning rib is 38.6 mm±10% and the lateral width of the positioning rib is 5.2 mm±10%.

21. The kit of claim 12, wherein the injection device comprises a medicament including at least one of glatiramer acetate, adalimumab, an anti-CGRP antibody, reslizumab, a follicle-stimulating hormone, or a substance for use in treatment or prevention of a disorder that affects dexterity of a user.

22. A kit comprising a packaging and an injection device, wherein the injection device defines a delivery window for visual feedback of medicament delivery and comprises a medicament,
wherein the packaging comprises:
- a channel extending longitudinally to accommodate the injection device, the channel including a first longitudinal wall, a second longitudinal wall opposing the first longitudinal wall, and a base wall extending between the first longitudinal wall and the second longitudinal wall;
- a first handling recess defined by the first longitudinal wall and a second handling recess defined by the second longitudinal wall; and
- a positioning rib protruding from the base wall into the channel, the positioning rib having a length in the longitudinal direction that is greater than a width in the lateral direction, wherein, when the injection device is in the channel, the delivery window accommodates the positioning rib.

23. The kit of claim 22, wherein a lateral position of the positioning rib is central in the channel and a longitudinal position of the positioning rib is eccentric in the channel.

24. The kit of claim 22, wherein the injection device has a circular cross section along the longitudinal direction.

25. The kit of claim 22, wherein the injection device further comprises a label longitudinally offset from the positioning rib, and wherein, when the injection device is in the channel, the label is visible from a planform of the packaging.

26. The kit of claim 22, wherein the injection device comprises a further positioning recess longitudinally aligned and circumferentially opposed the delivery window.

27. The kit of claim 22, wherein the first longitudinal wall or the second longitudinal wall comprises a grip for gripping of the packaging.

28. The kit of claim 22, wherein the longitudinal length of the positioning rib is 38.6 mm±10% and the lateral width of the positioning rib is 5.2 mm±10%.

29. The kit of claim 22, wherein the medicament includes at least one of glatiramer acetate, adalimumab, an anti-CGRP antibody, reslizumab, a follicle-stimulating hormone, or a substance for use in treatment or prevention of a disorder that affects dexterity of a user.

* * * * *